(12) United States Patent
Takaoka

(10) Patent No.: US 7,236,251 B2
(45) Date of Patent: Jun. 26, 2007

(54) OPTICAL SYSTEM AND OPTICAL APPARATUS CAPABLE OF SWITCHING BETWEEN OPTICAL COHERENCE TOMOGRAPHY OBSERVATION AND OPTICAL COHERENCE MICROSCOPY OBSERVATION

(75) Inventor: Hideyuki Takaoka, Hachioji (JP)

(73) Assignee: Olympus Corporation, Tokyo (JP)

( * ) Notice: Subject to any disclaimer, the term of this patent is extended or adjusted under 35 U.S.C. 154(b) by 766 days.

(21) Appl. No.: 10/006,621

(22) Filed: Dec. 10, 2001

(65) Prior Publication Data

US 2002/0048025 A1 Apr. 25, 2002

(30) Foreign Application Priority Data

Dec. 8, 2000 (JP) ............................. 2000-374085

(51) Int. Cl.
*G01B 9/02* (2006.01)
(52) U.S. Cl. ....................... 356/497; 356/479
(58) Field of Classification Search ................ 356/479, 356/497; 385/12; 250/227.19, 227.27
See application file for complete search history.

(56) References Cited

U.S. PATENT DOCUMENTS 5,321,501 A 6/1994 Swanson et al.

6,111,645 A * 8/2000 Tearney et al. ............. 356/484

OTHER PUBLICATIONS

Izatt et al., "Optical Coherence Microscopy in Scattering Media," Optics Letters, vol. 19, No. 8, Apr. 15, 1994, pp. 590-592.
IZatt et al., Optical Coherence tomography for Biodiagnostics, Optics & Photonics News, May 1997, pp. 41-47, 65.

* cited by examiner

*Primary Examiner*—Samuel A. Turner
(74) *Attorney, Agent, or Firm*—Pillsbury Winthrop Shaw Pittman LLP

(57) ABSTRACT

An optical system and optical apparatus prevent degradation of the S/N ratio due to switching between OCT and OCM observation modes and attain a high S/N ratio in both the observation modes. The optical system includes a light source 1 and a light-branching member 2 for branching light from the light source 1 into a reference light path and a signal light path. An objective 3 is placed in the signal light path. A light-scanning system 5 scans light in the signal light path with respect to a sample 4 placed in the signal light path. A beam diameter changing optical system 6 changes the beam diameter of light entering or exiting the light-scanning system 5. A light-combining member 7 combines together the reference light path and the signal light path. A light-detecting element 8 detects light combined by the light-combining member 7.

14 Claims, 11 Drawing Sheets

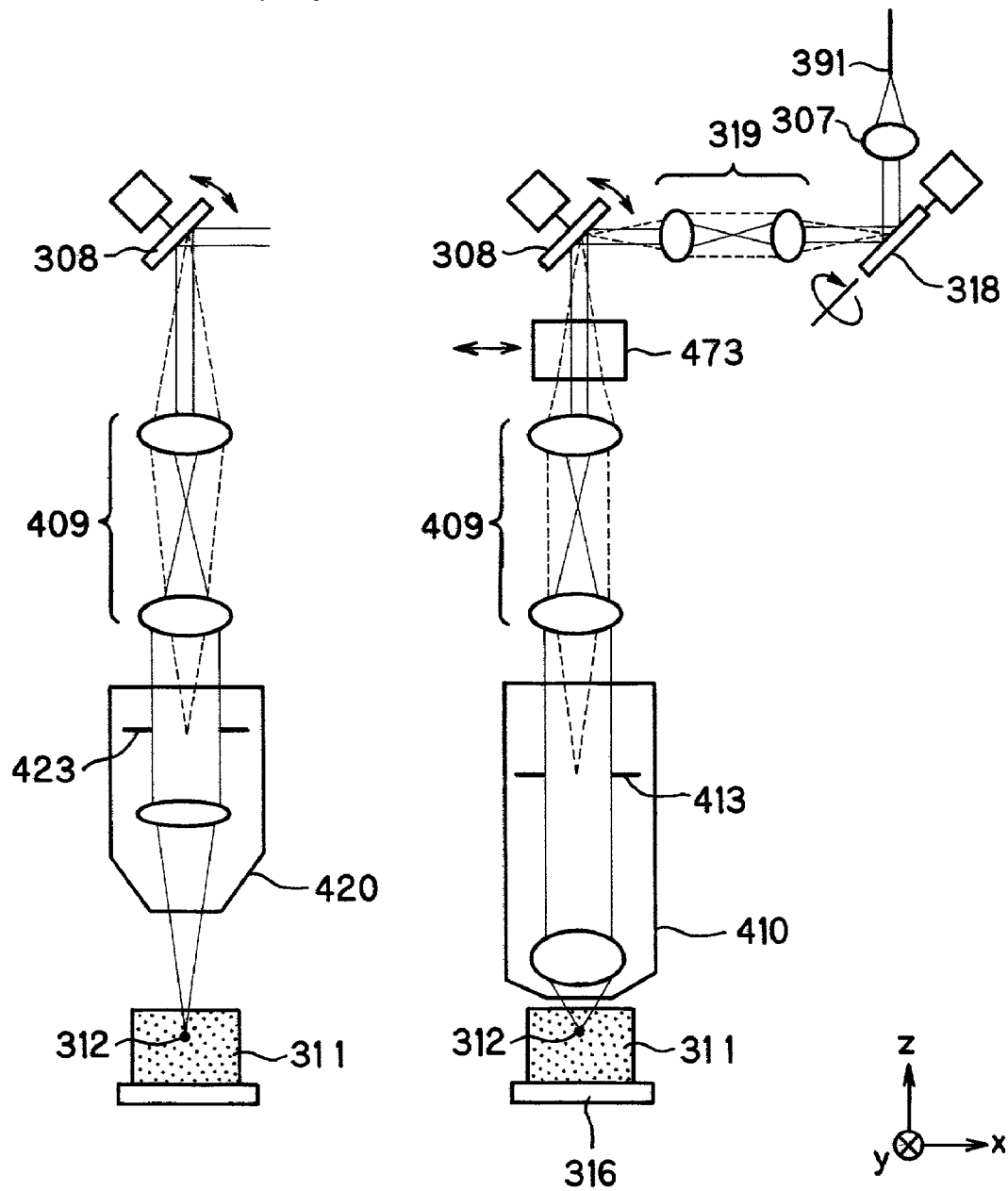

PRIOR ART

OPTICAL SYSTEM AND OPTICAL APPARATUS CAPABLE OF SWITCHING BETWEEN OPTICAL COHERENCE TOMOGRAPHY OBSERVATION AND OPTICAL COHERENCE MICROSCOPY OBSERVATION

This application claims benefit of Japanese Application Ser. No. 2000-374085 filed in Japan on Dec. 8, 2000, the contents of which are incorporated by this reference.

BACKGROUND OF THE INVENTION

1. Field of Invention

The present invention relates to an optical system and optical apparatus. More particularly, the present invention relates to an optical system and optical apparatus capable of switching between OCT (Optical Coherence Tomography) observation and OCM (Optical Coherence Microscopy) observation.

2. Discussion of Related Art

A scanning optical microscope having a confocal optical system disclosed in Japanese Patent Application Unexamined Publication (KOKAI) No. Sho 61-219919 is known as an optical apparatus that allows observation of the inside of a biological sample. Japanese Patent Application Unexamined Publication (KOKAI) No. Hei 4-146410 states techniques relating to a scanning optical system whereby the beam diameter of light incident on an objective is changed and the position of a scanning mirror is adjusted in accordance with the size and position of the pupil of the objective.

Recently, a technique called "low-coherence interferometry" or OCT (Optical Coherence Tomography)" such as that disclosed in U.S. Pat. No. 5,321,501 has become known as a method that allows observation of the inside of an opaque scattering sample, e.g. a biological tissue. FIG. 11 shows a general optical system for the low-coherence interferometry. Light from a light source 81 with a short coherence length is split by a beam splitter 82 between a signal light path leading to a sample 4 and a reference light path leading to a reflecting mirror 83. Light going and returning along the signal light path and the reference light path are recombined in the beam splitter 82. At this time, because the signal light path forms an optical path length substantially equal to that of the reference light path at an observation point 86 in the sample 4, only light scattered back from a region at the observation point 86 within a range in the optical axis direction that is substantially equal to the coherence length interferes with the reference light. Accordingly, by detecting the resulting interference signal with a detector 84, information about the inside of the sample 4 can be selectively obtained in the optical axis direction.

In general, the reflecting mirror 83 in the reference light path is moved in the optical axis direction, thereby performing scanning in the direction of depth of the sample 4 and, at the same time, producing a Doppler shift in the reference light. With the low-coherence interferometry, in general, heterodyne interferometric measurement is carried out to detect a beat signal having a Doppler shift frequency in the interference signal. Therefore, the measurement can be performed with a very high S/N ratio.

By performing scanning also in a direction perpendicular to the optical axis with a scanning mirror, an image of the xz-section in FIG. 11 can be obtained. If the depth of focus of the objective is set greater than the movable range of the reflecting mirror in the reference light path, the resolution in the xy-plane can be kept substantially constant despite the movement of the reflecting mirror. If the reflecting mirror is moved at high speed, image acquisition can be performed at high speed. In this case, an objective having a small numerical aperture is used because a large depth of focus is needed.

Meanwhile, a microscopic observation method using a confocal optical system with an objective having a large numerical aperture is known as a low-coherence interferometric technique, as shown in "Optics Letters, Vol. 19, No. 8, p. 590 (1994). The observation method is known as "OCM (Optical Coherence Microscopy)", which is a microscopic technique in which the high spatial resolution of the confocal optical system and the high S/N ratio of the low-coherence interferometry are combined together. In OCT, the coherence length is short in comparison to the depth of focus of the objective, whereas in OCM the depth of focus of the objective is equal to or less than the coherence length. OCM makes good use of the merit that the resolution in the xy-plane in FIG. 11 is high, and uses scanning mirrors for both the x- and y-directions to perform scanning in directions perpendicular to the optical axis, thereby making it possible to obtain a high-resolution image of the xy-plane. OCM also allows the inside of a living body to be observed at high resolution by making use of heterodyne interferometric measurement as in the case of OCT. The technical features of OCT and OCM are also stated in "Optics & Photonics News" May, p. 41 (1997).

As has been described above, OCT allows observation over a wide range in the direction of depth of the sample (in the z-direction). However, OCT is incapable of observing the sample with high resolution at a position of certain depth. Conversely, OCM allows the sample to be observed with high resolution at a position of certain depth but suffers from the problem that it takes a great deal of time to find a desired depth position because the depth of focus is shallow.

SUMMARY OF THE INVENTION

The present invention was made in view of the above-described problems. Accordingly, an object of the present invention is to provide an optical system and optical apparatus capable of readily finding a position (depth position) in a sample at which the user wants to observe the sample, and still allowing observation with high resolution and high S/N ratio at the desired depth position.

To attain the above-described object, the present invention provides an optical system including a light source and a light-branching member having a boundary surface for branching light from the light source into a reference light path and a signal light path. A scanning system moves light from the light source and a sample relative to each other. A light-combining member has a boundary surface for combining together the reference light path and the signal light path. A light-detecting element detects light combined by the light-combining member. A beam diameter changing optical system is placed between the light-branching member and the objective.

Another present invention provided an optical system including a light source and a light-branching member having a boundary surface for branching light from the light source into a reference light path and a signal light path. A pupil relay optical system is placed in the signal light path to relay the pupil of an objective (objective lens). A light-scanning system is placed in the signal light path in the vicinity of the position of the pupil relayed by the pupil relay optical system. A correcting mechanism makes the position of the relayed pupil and the light-scanning system approximately coincident with each other. A light-combining member has a boundary surface for combining together the reference light path and the signal light path. A light-detecting element detects light combined by the light-combining member.

Another present invention provides an optical apparatus including a light source and a light-branching member having a boundary surface for branching light from the light source into a reference light path and a signal light path. At least one objective (objective lens) is placed in the signal light path. A scanning system moves light collected by the objective and a sample relative to each other. A light-combining member has a boundary surface for combining together the reference light path and the signal light path. A light-detecting element detects light combined by the light-combining member. An optical path length control mechanism is placed between the light-branching member and the light-combining member to vary the optical path length. The optical apparatus further includes a scanning control mechanism. The scanning system has, at least, a first scanning mechanism for moving the collected light and the sample relative to each other in a first direction parallel to the optical axis of the objective, and a second scanning mechanism for moving the collected light and the sample relative to each other in a second direction perpendicular to the first direction. The scanning control mechanism has the function of choosing between the first scanning mechanism and the optical path length control mechanism, and the function of determining the scanning speed of the chosen mechanism and that of the second scanning mechanism.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIGS. 1(a) and 1(b) are diagrams showing the arrangement of an optical system according to the present invention that has a beam diameter changing optical system, of which: FIG. 1(a) shows the optical system when the beam diameter of incident light and that of emergent light are the same; and FIG. 1(b) shows the optical system when the beam diameter of emergent light is made larger than that of incident light by the beam diameter changing optical system.

FIGS. 5(a) and 5(b) are diagrams showing the arrangement of an optical system according to Example 1, of which: FIG. 5(a) shows the arrangement when an objective for OCT is used; and FIG. 5(b) shows the arrangement when an objective for OCM is used.

FIGS. 6(a) and 6(b) are diagrams showing the arrangement of an optical apparatus according to Example 2, of which: FIG. 6(a) shows the arrangement when an objective for OCM is used in the optical system; and FIG. 6(b) shows the arrangement when an objective for OCT is used in the optical system.

FIGS. 7(a) and 7(b) are diagrams showing the arrangement of an optical apparatus according to Example 3, of which: FIG. 7(a) shows the arrangement when an objective for OCM is used in the optical system; and FIG. 7(b) shows the arrangement when an objective for OCT is used in the optical system.

FIGS. 8(a) and 8(b) are diagrams showing the arrangement of a part of an optical apparatus according to Example 4, of which: FIG. 8(a) shows the arrangement when the relayed pupil position has been corrected by a correcting mechanism; and FIG. 8(b) shows the arrangement when the correcting mechanism is not present.

DETAILED DESCRIPTION

As has been stated above, OCT is suitable for performing observation over a wide range in the direction of depth of a sample (i.e. in the z-direction) by using an objective (objective lens) having a small numerical aperture and, in general, low magnification. On the other hand, OCM is suitable for observing the inside of a biological sample at high resolution by using in general a confocal optical system and an objective having a large numerical aperture and high magnification. Accordingly, a technique that allows OCT and OCM to be readily switched from one to another to observe the inside of a sample will be extremely useful. For example, the technique may be effectively used in a case where after a large structure in the sample has been located or a positional relationship between various regions in the sample has been detected, a region of interest in the sample is observed at higher resolution.

Figure 1A:
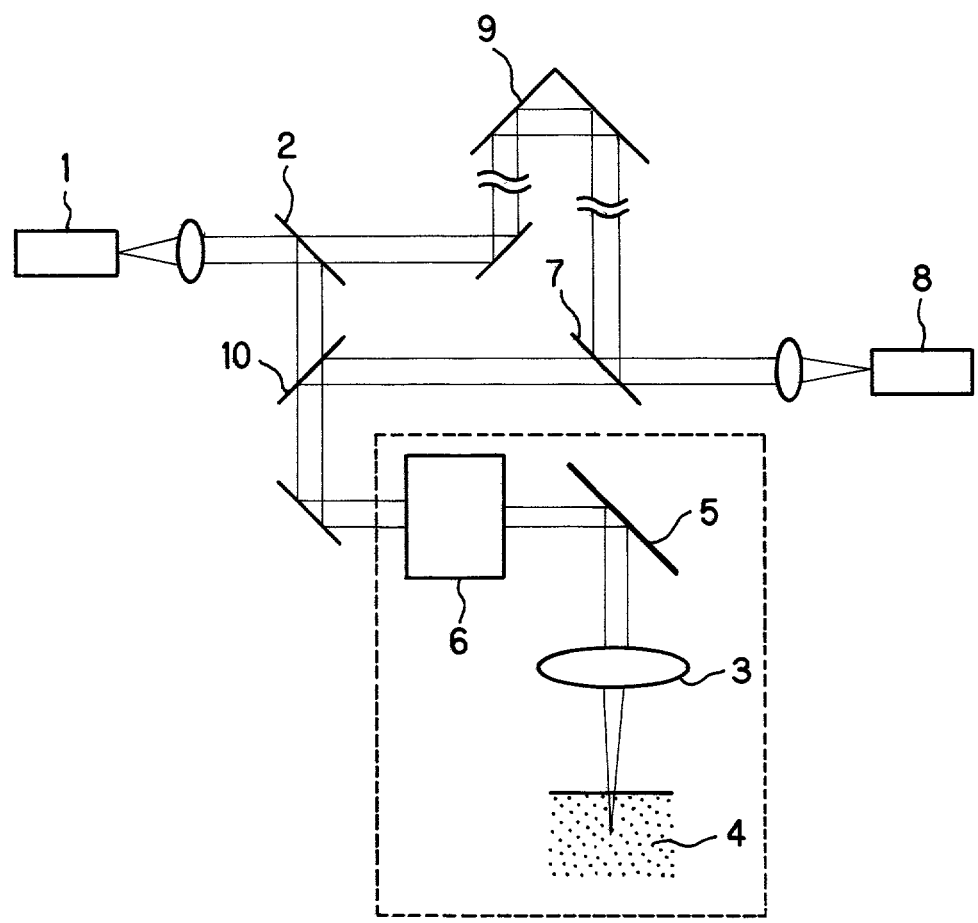

FIG. 1(a) is a diagram showing the arrangement of an optical system according to the present invention. The figure shows an optical system that allows OCT and OCM to be readily switched from one to another to perform observation. The arrangement and operation of the optical system according to the present invention will be described below with reference to the figure.

Light from a light source 1 is branched into a reference light path and a signal light path by a light-branching member 2. In FIG. 1(a), the reference light path is an optical path passing through the light-branching member 2 and extending via a turn-back mirror 9. The signal light path is an optical path reflected by the light-branching member 2. Light reflected by the light-branching member 2 passes through a half-mirror 10 and is applied to a sample 4 through a beam diameter changing optical system 6, a light-scanning system 5 and an objective 3. Light reflected and scattered by the sample 4 passes through the objective (objective lens) 3, the light-scanning system 5 and the beam diameter changing optical system 6 and is reflected by the half-mirror 10. The reference light path and the signal light path are combined together by a light-combining member 7, and the combined light is detected by a light-detecting element 8.

As has been stated above, OCT and OCM are largely different in the sample-side depth of focus from each other. Therefore, at least two optical systems having different numerical apertures are needed to perform observation in both the OCT and OCM modes. For this reason, the optical system according to the present invention has the beam diameter changing optical system 6 placed therein to allow an optimum beam diameter to be set for each of the optical systems having different numerical apertures.

Figure 1B:
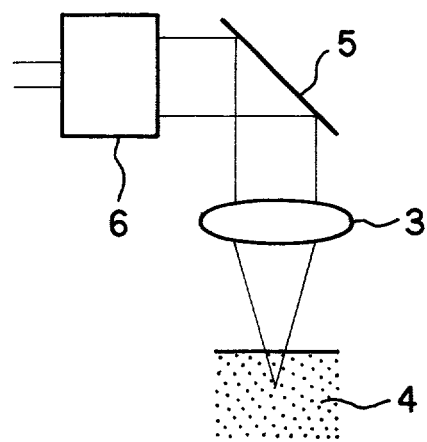

The beam diameter changing optical system 6 can change the beam diameter of light incident on the objective 3. Therefore, when the beam diameter is reduced by the beam diameter changing optical system 6, as shown in FIG. 1(*a*), the practical numerical aperture of the objective 3 decreases. When the beam diameter is increased by the beam diameter changing optical system 6, the arrangement within the dotted line in FIG. 1(*a*) can be changed to an arrangement that increases the numerical aperture of the objective 3 as shown in FIG. 1(*b*). Accordingly, when an OCT observation mode using an objective 3 of small numerical aperture and an OCM observation mode using an objective 3 of large numerical aperture are switched from one to another, for example, an optimum beam diameter can be set by using the above-described arrangement. Thus, the objectives 3 can be changed from one to another without loss of light quantity in either of the observation modes.

In particular, when a biological sample or the like is observed by the low-coherence interferometry or other similar method, light returning from the sample 4 is feeble. Therefore, a reduction in light utilization efficiency has to be avoided the most. The use of the arrangement according to the present invention makes it possible to set an optimum beam diameter for each of various objectives 3. Accordingly, high light utilization efficiency can be attained at all times. Thus, it becomes possible to perform observation with a high S/N ratio.

It should be noted that the light-branching member 2 and the light-combining member 7 are optical elements each having a boundary surface that branches incident light into transmitted light and reflected light, as in the case of a half-mirror, a beam splitter, or a fiber coupler. The beam diameter changing optical system 6 may be a pupil relay optical system arranged to relay the pupil of the objective 3. With this arrangement, it also becomes possible to place the light-scanning system 5 at a position conjugate to the pupil position of the objective 3.

In FIG. 1(*a*), light collected by the objective 3 is scanned in a direction perpendicular to the optical axis of the objective 3 by the light-scanning system 5. However, the arrangement may be such that the light-scanning system 5 is replaced with a fixed mirror, and a stage holding the sample 4 is moved in a direction perpendicular to the optical axis.

Next, an arrangement in which objectives are changed from one to another will be described as another example of switching numerical apertures from one to another. When light is scanned in a direction perpendicular to the optical axis of the objective, it is desirable to perform mirror scanning at the pupil position of the objective or at a position conjugate to the pupil position. In general, however, the pupil size of objectives differs for each objective. Therefore, with an optical system in which the beam diameter is constant at all times, a desired numerical aperture cannot be obtained when the beam diameter is smaller than the pupil. Conversely, when the beam diameter is larger than the pupil, the light utilization efficiency reduces undesirably.

In this regard, the optical system according to the present invention has the beam diameter changing optical system 6 and hence allows the diameter of the incident light beam to coincide with the pupil diameter of each particular objective. Accordingly, the above-described problems will not arise. Further, even when the OCT observation mode and the OCM observation mode are switched from one to another by changing objectives, there is no loss of the high S/N ratio, which is a feature of the low-coherence interferometry.

Figure 2:
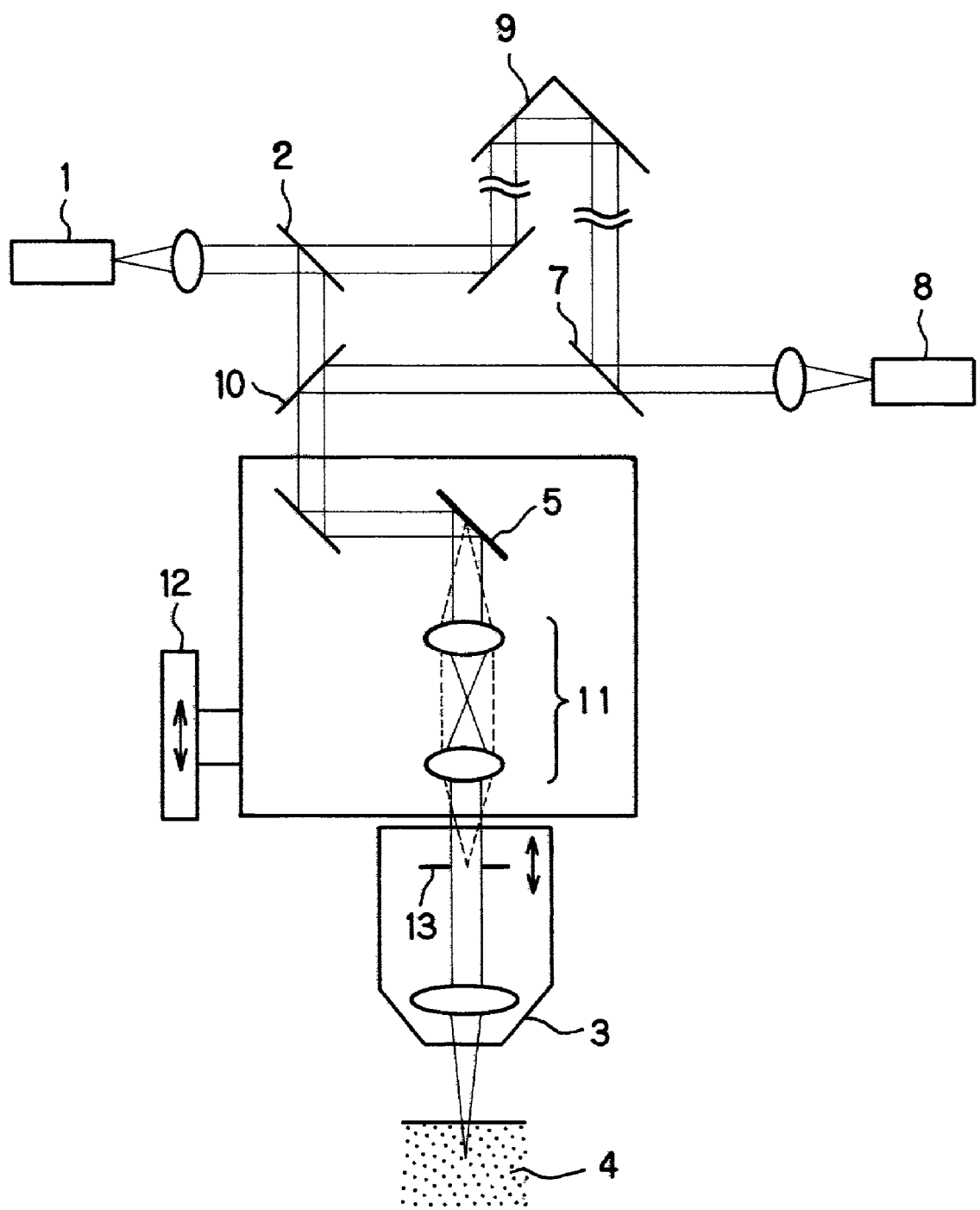
FIG. 2 is a diagram showing the arrangement of an optical system according to the present invention that has a relayed pupil position correcting mechanism.

FIG. 2 shows the arrangement of another optical system according to the present invention. The arrangement differs from FIG. 1 in the structure of an optical system extending from the half-mirror 10 to the sample 4 in the signal light path. In FIG. 2, light of the signal light path passing through the half-mirror 10 is scanned by the light-scanning system 5. Then, the light passes through a pupil relay optical system 11 and is applied to the sample 4 by the objective 3. The pupil relay optical system 11 relays the pupil 13 of the objective 3. The light-scanning system 5 is placed at the conjugate position of the pupil 13 relayed by the pupil relay optical system 11.

Let us assume that objective swapping is performed in the illustrated state to place another objective in the optical path instead of the objective 3. In general, the pupil position of objectives differs for each objective. In this case also, the pupil position of the newly placed objective differs from the position of the pupil 13 of the former objective 3. Consequently, although the pupil of the newly placed objective is relayed by the pupil relay optical system 11, it may be relayed to a position different from the position of the light-scanning system 5. Therefore, the optical system according to the present invention is provided with a correcting mechanism 12 whereby the position of the pupil newly relayed by the pupil relay optical system 11 and the position of the light-scanning system 5 are made coincident with each other.

In FIG. 2, the correcting mechanism 12 has a moving mechanism (not shown). The moving mechanism causes the pupil relay optical system 11 and the light-scanning system 5 to move together as one unit. Accordingly, even when the objective 3 is replaced with another, the position of the relayed pupil of the objective and the position of the light-scanning system 5 can be made coincident with each other. Consequently, there is no possibility of the light beam being eclipsed by the pupil 13 during scanning of light performed by the light-scanning system 5. Thus, it is possible to prevent deficiency of the marginal illumination.

It should be noted that the optical systems shown in FIGS. 1(*a*) and 2 may be arranged as follows. The optical path extending from the light-branching member 2 to the light-combining member 7, that is, the reference light path or the signal light path or each of them, may be provided with a frequency modulating member for modulating the frequency of light, e.g. an acousto-optic modulator (AOM). With this arrangement, it is possible to perform heterodyne measurement utilizing the frequency difference between light passing through the reference light path and light passing through the signal light path and hence possible to obtain an observation image with high S/N ratio.

The reference light path or the signal light path or each of them may be provided with an optical path length control mechanism for varying the optical path length. With this arrangement, it becomes possible to adjust the depth position of the observation point in the sample or to perform scanning in the direction of depth of the sample.

The optical path length control mechanism may be arranged to be capable of modulating the frequency of light. Thus, the optical path length control mechanism can also perform the function of a frequency modulating member.

The optical system may have a signal processing unit for obtaining a signal having a difference frequency component corresponding to the frequency difference between light passing through the reference light path and light passing through the signal light path.

Both the frequency modulating member and the optical path length control mechanism can produce a difference in frequency between light passing through the signal light path and light passing through the reference light path. Among signals detected by the light-detecting element, a signal having a frequency component corresponding to the frequency difference is obtained by using the signal processing unit, thereby allowing heterodyne detection to be performed.

Figure 3:
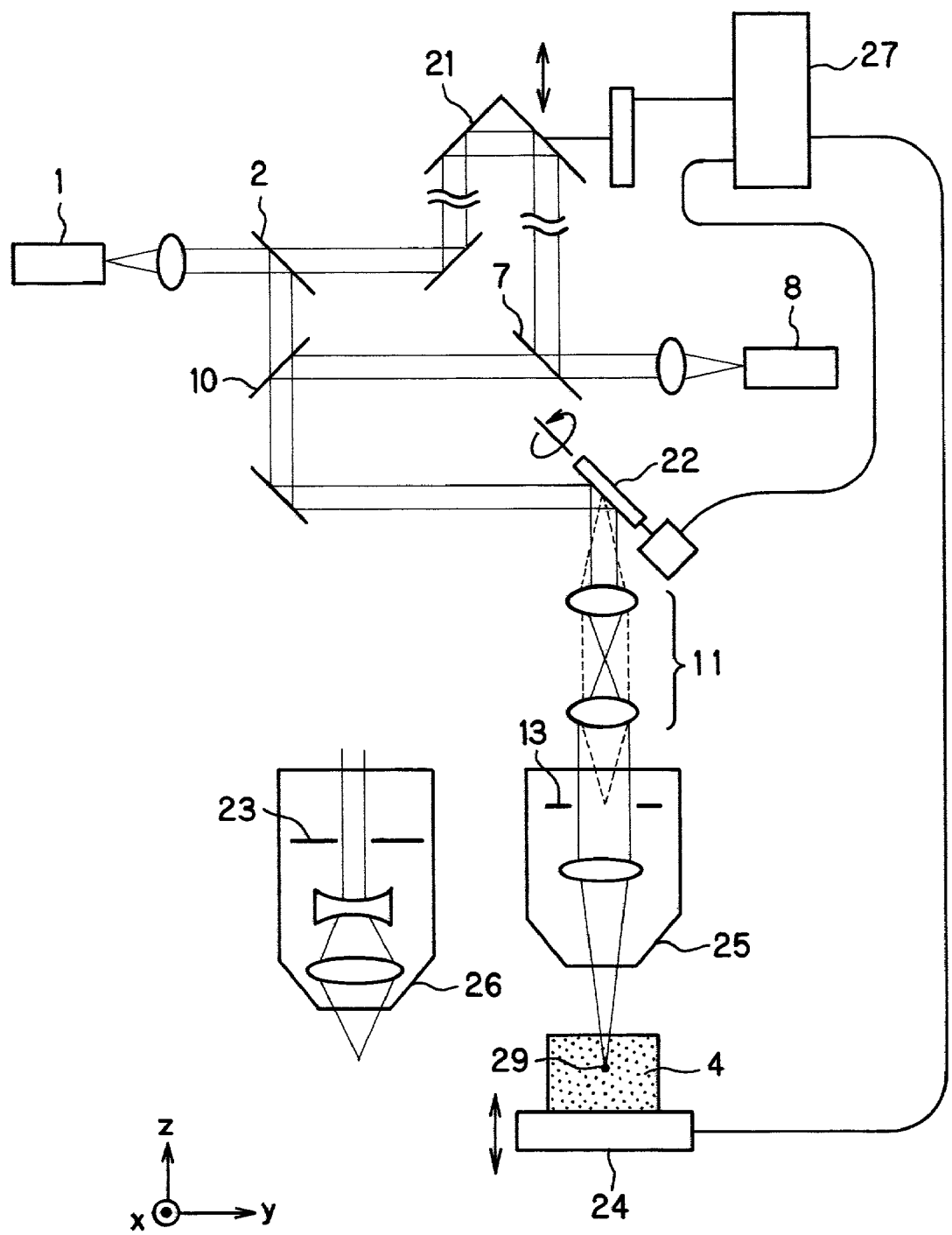
FIG. 3 is a diagram showing the arrangement of an optical apparatus according to the present invention.

FIG. 3 shows the arrangement of an optical apparatus according to the present invention. Light from a light source 1 is branched into a reference light path and a signal light path by a light-branching member 2. Light in the reference light path passing through the light-branching member 2 travels via an optical path length control mechanism 21 to reach a light-combining member 7. Meanwhile, light in the signal light path reflected by the light-branching member 2 passes through a half-mirror 10 and is reflected by a light-scanning system 22 so as to be applied to a sample 4 through an objective 25 or 26. The sample 4 is held on a scanning stage 24. Light reflected and scattered at an observation point (i.e. a position where light is collected by the objective) 29 in the sample 4 passes through the objective 25 or 26 and via the light-scanning system 22 and is reflected by the half-mirror 10 to reach the light-combining member 7. Light in the reference light path and light in the signal light path are combined together by the light-combining member 7, and the combined light is detected by a light-detecting element 8.

In the optical apparatus according to the present invention, the optical path length control mechanism 21 is placed in the reference light path so that the optical path length of the reference light path can be varied. More specifically, the optical path length control mechanism 21 has a reflection or transmission type optical element and a moving mechanism so that the optical path length is varied by moving the optical element through the moving mechanism. Varying the optical path length of the reference light path causes a change in the position within the sample 4 at which the optical path length of the signal light path and that of the reference light path coincide with each other. Thus, the optical path length control mechanism 21 causes the observation point 29 in the sample 4 to move relative to the sample 4 in a direction (first direction) along the optical axis of the objective 25.

The scanning system comprises the light-scanning system 22 and the scanning stage 24. The scanning stage 24 is a first scanning mechanism for moving the sample 4 in the first direction. The light-scanning system 22 is a second scanning mechanism for moving the observation point 29 in the sample 4 in a direction (second direction) perpendicular to the optical axis of the objective 25. Accordingly, in the arrangement shown in FIG. 3, the first direction corresponds to the z-direction. The second direction corresponds to the x-direction. It should be noted that the pupil 13 (23) of the objective 25 (26) is relayed to the position of the light-scanning system 22 by a pupil relay optical system 11. The difference in the pupil position between the pupils 13 and 23 of the objectives 25 and 26 is compensated by the correcting mechanism 12 shown in FIG. 2.

A scanning control mechanism 27 has the function of controlling the respective scanning speeds of the light-scanning system 22 and the scanning stage 24 and the moving speed (scanning speed) of the optical element in the optical path length control mechanism 21. The scanning control mechanism 27 further has the function of choosing between the scanning stage 24 and the optical path length control mechanism 21 as a scanning mechanism for the first direction.

The foregoing is the basic arrangement of an optical apparatus according to the present invention. As objectives, it is preferable to use at least one objective having a numerical aperture that satisfies the condition of $Lc \geq Df$. In the condition $Lc \geq Df$, $Df$ is a value generally known as the depth of focus, which is obtained from $Df = \lambda c/(NA)^2$, where $NA$ is the numerical aperture of the objective, and $\lambda c$ is the center wavelength of the light source. $Lc$ is the coherence length of light incident on the sample.

In addition to the objective having a numerical aperture satisfying the condition of $Lc \geq Df$, the optical apparatus may have at least one objective having a numerical aperture that satisfies the condition of $Lc < Df$. When the optical apparatus has both the objective satisfying the condition of $Lc \geq Df$ and the objective satisfying the condition of $Lc < Df$, the scanning control mechanism 27 sets optimum scanning speeds and chooses an optimum scanning mechanism for the first direction in accordance with the selection of either of the objectives.

Let us explain the objectives, the objective 25 is an objective having a numerical aperture satisfying the condition of $Lc < Df$. The depth of focus of the objective 25 is longer than the coherence length of light from the light source 1 that is incident on the sample 4. Therefore, the objective 25 is suitable for observation by OCT. On the other hand, the objective 26 is an objective having a numerical aperture satisfying the condition of $Lc \geq Df$. The numerical aperture of the objective 26 is larger than that of the objective 25. The objective 26 is suitable for observation by OCM.

It should be noted that the optical apparatus according to the present invention may be arranged such that the objective 25 is not used, but only the objective 26 is used, as will be described later. However, the optical apparatus is herein described as one that uses both the objectives 25 and 26 with a view to facilitating the explanation. It is also assumed for explanatory simplicity that light from the light source passes through the whole pupil of the objective so as to satisfy the numerical aperture of each objective. Accordingly, the objective 25 is used for OCT, and the objective 26 is for OCM.

Next, the operation of the scanning control mechanism 27 will be described. The scanning control mechanism 27 chooses between the scanning stage 24 and the optical path length control mechanism 21 as a scanning mechanism for the first direction according to the value of $Df$ of the objective used. Then, the scanning control mechanism 27 determines the scanning speed of the light-scanning system 22 and that of the chosen scanning mechanism for the first direction.

When $Lc < Df$, i.e. when the objective 25 is used, the optical apparatus is set in the OCT observation mode. In the OCT observation mode, the coherence length determines the resolution in the z-direction. Therefore, the scanning control mechanism 27 chooses the optical path length control mechanism 21 as a scanning mechanism for the first direction. Thus, the position in the sample 4 at which the optical path length of the signal light path and that of the reference light path coincide with each other is varied. At this time, there is no change in the relative positional relationship between the objective 25 and the sample 4. Assuming that the scanning speed of the optical element in the optical path length control mechanism 21 is v1 and the scanning speed of the light-scanning system 22 is v2, the scanning control mechanism 27 sets each scanning speed so that the condition of v1>v2 is satisfied.

Thus, when Lc<Df, the scanning speed of the optical path length control mechanism 21 (scanning speed in the first direction) is set faster than the scanning speed of the light-scanning system 22 (scanning speed in the second direction) to observe an image of the xz-section. It should be noted that fast scanning in the first direction is effective in obtaining a practical Doppler frequency in heterodyne interferometric measurement utilizing a Doppler frequency produced during scanning by the optical path length control mechanism 21.

When Lc≧Df, i.e. when the objective 26 is used, the optical apparatus is set in the OCM observation mode. In the OCM observation mode, the depth of focus is not greater than the coherence length. Therefore, it is necessary in order to scan the observation point 29 in the first direction to change the relative positional relationship between the objective 26 and the sample 4. Accordingly, the scanning control mechanism 27 chooses the scanning stage 24 as a scanning mechanism for the first direction. Assuming that the scanning speed of the scanning stage 24 is v1 and the scanning speed of the light-scanning system 22 is v2, the scanning control mechanism 27 sets each scanning speed so that the condition of v2>v1 is satisfied.

A scanning mirror may be used as a specific structure of the light-scanning system 22. When a scanning mirror is used, scanning by the scanning stage 24 is in general slower in speed than scanning by the scanning mirror. Therefore, the most efficient way of observing an xz-section image of the sample 4 at as high a speed as possible is to perform scanning in the second direction at a higher speed than in the first direction. In other words, it is desirable that the scanning speeds should be set so as to satisfy the condition of v2>v1.

Although in FIG. 3 the scanning stage 24 is moved to scan in the first direction, the mechanism may be arranged such that the scanning stage 24 is fixed and the objective 26 is moved in the first direction. The above-described setting of the scanning speeds is also preferable when scanning in the first direction is performed by moving the objective 26. In particular, when the observation range in the first direction is longer than the coherence length, the optical path length needs to be adjusted by the optical path length control mechanism 21 in accordance with the movement of the observation point 29 by the objective 26. Accordingly, the adjustment of the optical path length can be performed by setting the scanning speed v1 of the objective 26 lower than the scanning speed v2 of the light-scanning system 22.

Thus, the scanning control mechanism 27 sets scanning speeds and chooses a scanning mechanism for the first direction in accordance with the selection of an objective to be used, as follows:

When Lc<Df, v1>v2.
When Lc≧Df, v2>v1.

In the above conditions: Df is a value obtained from $Df=\lambda c/(NA)^2$, where NA is the numerical aperture of the objective placed in the signal light path, and $\lambda c$ is the center wavelength of the light source; Lc is the coherence length of light incident on the sample; and v1 and v2 are the scanning speed in the first direction and the scanning speed in the second direction, respectively.

In the arrangement shown in FIG. 3, the optical apparatus is switched between the OCT and OCM observation modes by changing the objectives 25 and 26 from one to another, for explanatory simplicity. With the basic arrangement of the optical apparatus according to the present invention, however, it is possible to perform observation in both the OCT and OCM modes with the objective 26 alone. For example, as the beam of light entering the objective 26 is narrowed, the effective numerical aperture decreases. Consequently, the objective 26 becomes practically the same as the objective 25. In this way, the optical apparatus can be arranged to allow observation in both the OCT and OCM modes with a single objective. It should be noted that the term "effective numerical aperture" means the sample-side numerical aperture determined by the beam diameter of light actually entering the objective 26.

In this case, the scanning control mechanism 27 sets scanning speeds and chooses a scanning mechanism for the first direction in accordance with the effective numerical aperture of an objective to be used, as follows:

When Lc<Df', v1>v2.
When Lc≧Df', v2>v1.

In the above conditions: Df' is a value obtained from $Df'=\lambda c/(NA')^2$, where NA' is the effective numerical aperture of the objective placed in the signal light path, and $\lambda c$ is the center wavelength of the light source; Lc is the coherence length of light incident on the sample; and v1 and v2 are the scanning speed in the first direction and the scanning speed in the second direction, respectively.

In the optical apparatus shown in FIG. 3, frequency modulation is effected by the optical path length control mechanism to perform heterodyne interferometric measurement. However, a frequency modulating member that causes no change in the optical path length, such as an acoustooptic element, may be provided separately from the optical path length control mechanism to perform heterodyne interferometric measurement. In this case, the arrangement of the optical apparatus is approximately the same as the arrangement shown in FIG. 3. The arrangement differs from the arrangement shown in FIG. 3 in that a frequency modulating member that modulates the frequency of light without causing a change in the optical path length is provided in the reference light path or the signal light path or each of them, and, regarding the operation of the scanning control mechanism 27, the scanning speeds are set so as to satisfy the condition of v2>v1 not only when Lc≧Df or Lc≧Df' but also when Lc<Df or Lc<Df'.

Frequency modulation can be performed by the optical path length control mechanism 21 as has been described above in connection with FIG. 3. However, with an arrangement wherein a turn-back mirror is driven as shown in FIG. 3, it is difficult to keep the modulation frequency constant over the whole optical path length control range. Therefore, the optical path length control mechanism 21 as shown in FIG. 3 may cause Doppler frequency broadening, which leads to degradation of the S/N ratio.

In contrast, a frequency modulating member such as an acoustooptic element performs frequency modulation that is constant at all times, and causes no change in the optical path length. Therefore, the optical path length control mechanism 21 need not perform frequency modulation. Further, even when Lc<Df', the scanning speeds can be set so as to satisfy the condition of v2>v1 as in the case of Lc≧Df'. Accordingly, the optical path length control mechanism 21 need not be driven at high speed. As has been stated above, a scanning mirror used as a specific structure of the light-scanning system 22 can be driven at high speed in general. Therefore, the structure of the present invention is particularly effective in observation that requires high time resolution.

Thus, if a frequency modulating member capable of modulating the frequency of light without causing a change in the optical path length is provided in the reference light path or the signal light path or each of them, it becomes unnecessary to provide a mechanical driving mechanism for frequency modulation. Accordingly, observation can be performed at higher speed in the above-described OCM observation mode, in particular. Thus, provision of such a frequency modulating member is favorable.

In this case, the scanning control mechanism 27 sets the scanning speeds so that the following condition is satisfied regardless of the size relation between Lc and Df or between Lc and Df', and chooses a scanning mechanism for the first direction:

v2>v1

It should be noted that the foregoing arrangement in which the scanning speeds are changed according to the value of Df or Df' of the objective used may also be provided with a frequency modulating member capable of modulating the frequency of light without causing a change in the optical path length in the reference light path or the signal light path or each of them.

Figure 4:
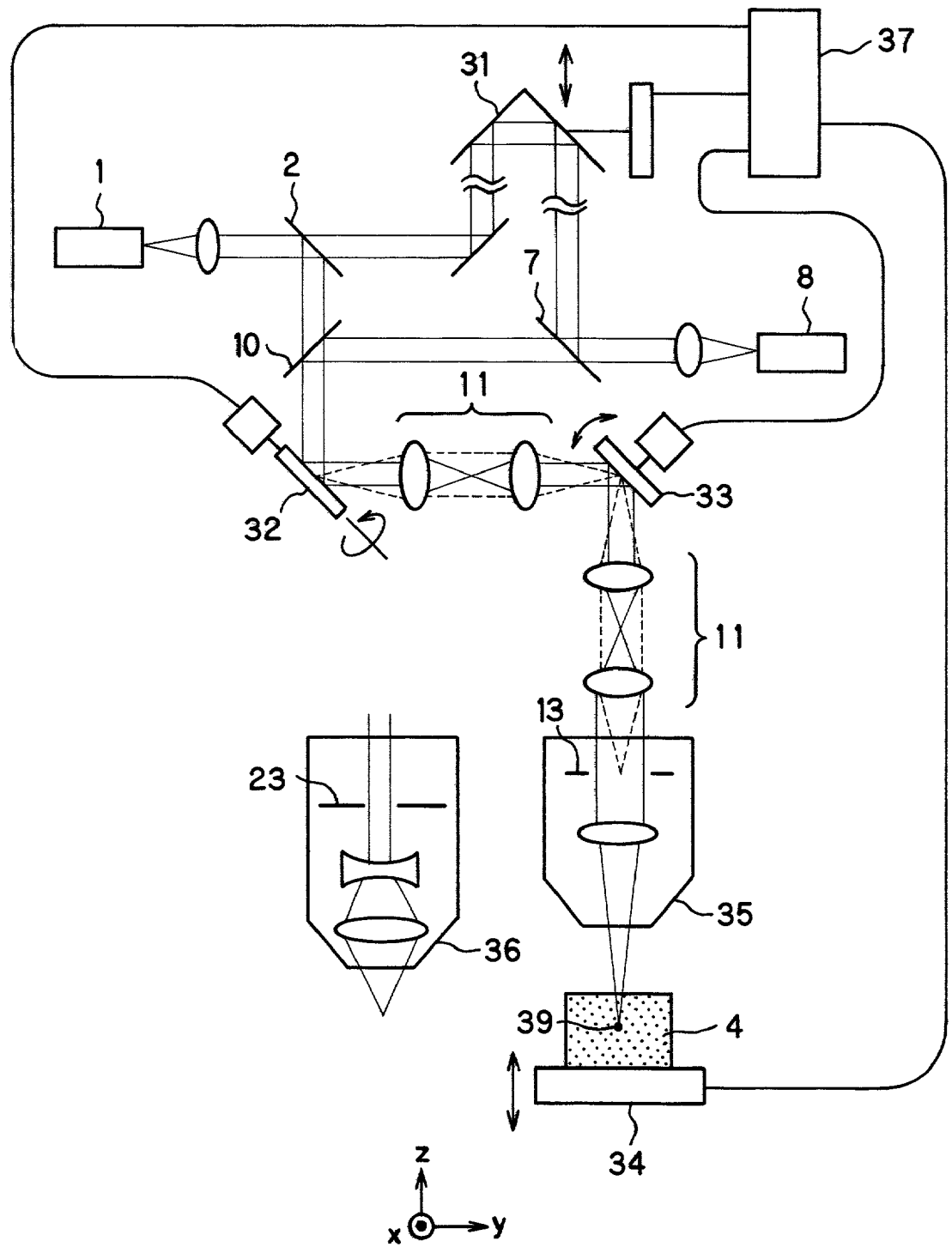
FIG. 4 is a diagram showing the arrangement of an optical apparatus according to the present invention that has a three-dimensionally expanded observation range.

FIG. 4 shows the arrangement of another optical system according to the present invention.

Light from a light source 1 is branched into a reference light path and a signal light path by a light-branching member 2. Light in the reference light path passing through the light-branching member 2 travels via an optical path length control mechanism 31 to reach a light-combining member 7. Meanwhile, light in the signal light path reflected by the light-branching member 2 passes through a half-mirror 10 and is reflected by a light-scanning system 32 for scanning light in the second direction. Light reflected by the light-scanning system 32 passes through a pupil relay optical system 11 and is incident on a light-scanning system 33 for scanning light in a third direction. Light reflected by the light-scanning system 33 passes through a pupil relay optical system 11 and enters an objective 35 or 36 through which the light is applied to a sample 4. The sample 4 is held on a scanning stage 34. Light reflected and scattered at an observation point (i.e. a position where light is collected by the objective) 39 in the sample 4 passes through the objective 35 or 36, the pupil relay optical systems 11 and the light-scanning systems 33 and 32 and is reflected by the half-mirror 10 to reach the light-combining member 7. Light in the reference light path and light in the signal light path are combined together by the light-combining member 7, and the combined light is detected by a light-detecting element 8.

The optical apparatus shown in FIG. 4 is also provided with an optical path length control mechanism 31 in the reference light path so that the optical path length of the reference light path can be varied. The scanning system comprises the light-scanning systems 32 and 33 and the scanning stage 34. The scanning stage 34 is a first scanning mechanism for moving the sample 4 in the first direction. The light-scanning system 32 is a second scanning mechanism for moving the observation point 39 in the sample 4 in a direction (second direction) perpendicular to the optical axis of the objective 35. The light-scanning system 33 is a third scanning mechanism for moving the observation point 39 in the sample 4 in a direction (third direction) perpendicular to both the first and second directions. Thus, in the arrangement shown in FIG. 4, the first direction corresponds to the z-direction. The second direction corresponds to the x-direction. The third direction corresponds to the y-direction. It should be noted that the pupil 13 (23) of the objective 35 (36) is relayed to the respective positions of the light-scanning systems 32 and 33 by the two pupil relay optical systems 11. The difference in the pupil position between the pupils 13 and 23 of the objectives 35 and 36 is compensated by the correcting mechanism 12 shown in FIG. 2.

A scanning control mechanism 37 has the function of controlling the respective scanning speeds of the light-scanning systems 32 and 33 and the scanning stage 34 and the moving speed (scanning speed) of the optical element in the optical path length control mechanism 31. The scanning control mechanism 37 further has the function of choosing between the scanning stage 34 and the optical path length control mechanism 31 as a scanning mechanism for the first direction.

The foregoing is the basic arrangement of another optical apparatus according to the present invention. As objectives, it is preferable to use at least one objective having a numerical aperture that satisfies the condition of $Lc \geq Df$. In the condition $Lc \geq Df$, Df is a value generally known as the depth of focus, which is obtained from $Df = \lambda c/(NA)^2$, where NA is the numerical aperture of the objective, and $\lambda c$ is the center wavelength of the light source. Lc is the coherence length of light incident on the sample.

In addition to the objective having a numerical aperture satisfying the condition of $Lc \geq Df$, the optical apparatus may have at least one objective having a numerical aperture that satisfies the condition of $Lc<Df$. When the optical apparatus has both the objective satisfying the condition of $Lc \geq Df$ and the objective satisfying the condition of $Lc<Df$, the scanning control mechanism 37 sets optimum scanning speeds and chooses an optimum scanning mechanism for the first direction in accordance with the selection of either of the objectives. When $Lc<Df$, i.e. when the objective 35 is used, the optical apparatus is set in the OCT observation mode. In the OCT observation mode, the coherence length determines the resolution in the z-direction. Therefore, the scanning control mechanism 37 chooses the optical path length control mechanism 31 as a scanning mechanism for the first direction. Thus, the position in the sample 4 at which the optical path length of the signal light path and that of the reference light path coincide with each other is varied. At this time, there is no change in the relative positional relationship between the objective 35 and the sample 4. Assuming that the scanning speed of the optical element in the optical path length control mechanism 31 is v1, and the scanning speed of the light-scanning system 32 is v2, and further the scanning speed of the light-scanning system 33 is v3, the scanning control mechanism 37 sets each scanning speed so that the condition of v1>v2>v3 is satisfied.

Thus, when $Lc<Df$, the scanning speed of the optical path length control mechanism 31 (scanning speed in the first direction) is set faster than the scanning speed of the light-scanning system 32 (scanning speed in the second direction) to observe an image of the xz-section. In addition, the scanning speed of the light-scanning system 33 (scanning speed in the third direction) is set slower than the scanning speed of the light-scanning system 32 to obtain an xz-section image for each scanning point in the y-direction. Thus, the optical apparatus shown in FIG. 4 can obtain a three-dimensional image of the sample 4. It should be noted that fast scanning in the first direction is effective in obtaining a practical Doppler frequency in heterodyne interferometric measurement utilizing a Doppler frequency produced during scanning by the optical path length control mechanism 31.

When $Lc \geq Df$, i.e. when the objective 36 is used, the optical apparatus is set in the OCM observation mode. In the OCM observation mode, the depth of focus is not greater than the coherence length. Therefore, it is necessary in order to scan the observation point 39 in the first direction to change the relative positional relationship between the objective 36 and the sample 4. Accordingly, the scanning control mechanism 37 chooses the scanning stage 34 as a scanning mechanism for the first direction. Assuming that the scanning speed of the scanning stage 34 is v1, and the scanning speed of the light-scanning system 32 is v2, and further the scanning speed of the light-scanning system 33 is v3, the scanning control mechanism 37 sets each scanning speed so that the condition of v2>v3>v1 is satisfied.

Thus, when Lc≧Df, the scanning speed of the scanning stage 34 (scanning speed in the first direction) is set slower than the scanning speed of the light-scanning system 32 (scanning speed in the second direction) and the scanning speed of the light-scanning system 33 (scanning speed in the third direction) to observe an xy-section image preferentially. After the acquisition of an xy-section image, the scanning stage 34 is moved to obtain an xy-section image at a new z-position. Thus, a three-dimensional image of the sample 4 is obtained.

A scanning mirror may be used as a specific structure of each of the light-scanning systems 32 and 33. When a scanning mirror is used, scanning by the scanning stage 34 is in general slower in speed than scanning by the scanning mirror. Therefore, the most efficient way of observing a three-dimensional image of the sample 4 at as high a speed as possible is to perform scanning in the second and third directions at a higher speed than in the first direction. In other words, it is desirable that the scanning speeds should be set so as to satisfy the condition of v2>v3>v1.

As has been stated in connection with the optical apparatus shown in FIG. 3, the mechanism may be arranged such that the scanning stage 34 is fixed and the objective 36 is moved in the first direction. The above-described setting of the scanning speeds is also preferable when scanning in the first direction is performed by moving the objective 36. In particular, when the observation range in the first direction is longer than the coherence length, the optical path length needs to be adjusted by the optical path length control mechanism 31 in accordance with the movement of the observation point 39 by the objective 36. Accordingly, the adjustment of the optical path length can be performed by setting the scanning speed v1 of the objective 36 lower than the scanning speeds v2 and v3 of the light-scanning systems 32 and 33.

Thus, the scanning control mechanism 37 sets scanning speeds and chooses a scanning mechanism for the first direction in accordance with the selection of an objective to be used, as follows:

When Lc<Df, v1>v2>v3.
When Lc≧Df, v2>v3>v1.

In the above conditions: Df is a value obtained from $Df=\lambda c/(NA)^2$, where NA is the numerical aperture of the objective placed in the signal light path, and λc is the center wavelength of the light source; Lc is the coherence length of light incident on the sample; and v1, v2 and v3 are the scanning speed in the first direction, the scanning speed in the second direction and the scanning speed in the third direction, respectively.

In the above-described basic arrangement of another optical apparatus according to the present invention, it is also possible to perform observation in both the OCT and OCM modes with the objective 36 alone. As has been described in connection with the optical apparatus shown in FIG. 3, the beam of light entering the objective 36 is narrowed to reduce the effective numerical aperture. As a result, the objective 36 becomes practically the same as the objective 35 for use in the OCT observation mode. Thus, the optical apparatus can be arranged to allow observation in both the OCT and OCM modes with a single objective.

In this case, the scanning control mechanism 37 sets scanning speeds and chooses a scanning mechanism for the first direction in accordance with the effective numerical aperture of an objective to be used, as follows:

When Lc<Df', v1>v2>v3.
When Lc≧Df', v2>v3>v1.

In the above conditions: Df' is a value obtained from $Df'=\lambda c/(NA')^2$, where NA' is the effective numerical aperture of the objective placed in the signal light path, and λc is the center wavelength of the light source; Lc is the coherence length of light incident on the sample; and v1, v2 and v3 are the scanning speed in the first direction, the scanning speed in the second direction, and the scanning speed in the third direction, respectively.

Further, the reference light path or the signal light path or each of them may be provided with a frequency modulating member capable of modulating the frequency of light without causing a change in the optical path length. Provision of such a frequency modulating member eliminates the need for the optical path length control mechanism 31 to perform frequency modulation, as has been described in connection with the optical apparatus shown in FIG. 3. Accordingly, the scanning control mechanism 37 sets scanning speeds and chooses a scanning mechanism for the first direction in accordance with the numerical aperture or effective numerical aperture of an objective to be used, as follows:

When Lc<Df or Lc<Df', v2>v1>v3 or v2>v3>v1.
When Lc≧Df or Lc≧Df', v2>v3>v1.

In the above conditions: Df is a value obtained from $Df=\lambda c/(NA)^2$ where NA is the numerical aperture of the objective placed in the signal light path, and λc is the center wavelength of the light source; Df' is a value obtained from $Df'=\lambda c/(NA')^2$, where NA' is the effective numerical aperture of the objective placed in the signal light path, and λc is the center wavelength of the light source; Lc is the coherence length of light incident on the sample; and v1, v2 and v3 are the scanning speed in the first direction, the scanning speed in the second direction, and the scanning speed in the third direction, respectively.

Thus, if a frequency modulating member capable of modulating the frequency of light without causing a change in the optical path length is provided in the reference light path or the signal light path or each of them, observation can be performed at higher speed in the above-described OCM observation mode, in particular. As has been stated above, a scanning mirror used as a specific structure of each of the light-scanning systems 32 and 33 can be driven at high speed in general. Therefore, the above-described arrangement is particularly effective in observation that requires high time resolution.

Further, the optical apparatus shown in FIG. 3 or 4 may be provided with a beam diameter changing optical system for changing the diameter of a light beam. In this case, the beam diameter changing optical system should preferably be disposed at a position where light enters or exits a light-scanning system. With this arrangement, it is possible to set a desired effective numerical aperture in both the OCT and OCM observation modes or to prevent the light utilization efficiency from lowering when objectives are changed from one to another.

The beam diameter changing optical system may be a pupil relay optical system arranged to relay the pupil of the objective. With this arrangement, it also becomes possible to place a scanning system for performing scanning in the second or third direction at a position conjugate to the pupil position of the objective.

Further, the optical apparatus may be provided with a correcting mechanism for making the position of the objective pupil relayed by the pupil relay optical system and the position of the light-scanning system approximately coincident with each other. With this arrangement, even when objective swapping results in displacement of the pupil position of the newly placed objective from the pupil position of the former objective, the position of the relayed pupil and the position of the light-scanning system can be made substantially coincident with each other. Thus, the light-scanning system for performing scanning in the second or third direction can be always placed at a position conjugate to the pupil position of the objective, and deficiency of the marginal illumination can be prevented.

Further, a change in the effective numerical aperture of the objective and a change in the optical system incidental to the effective numerical aperture change may produce a difference in dispersion characteristics between the signal light path and the reference light path. Therefore, it is desirable to provide a dispersion adjusting element for compensating for the difference in dispersion characteristics. It is preferable that the dispersion adjusting element should be capable of selectively or continuously controlling the amount of dispersion adjustment made by it.

Figure 10A:
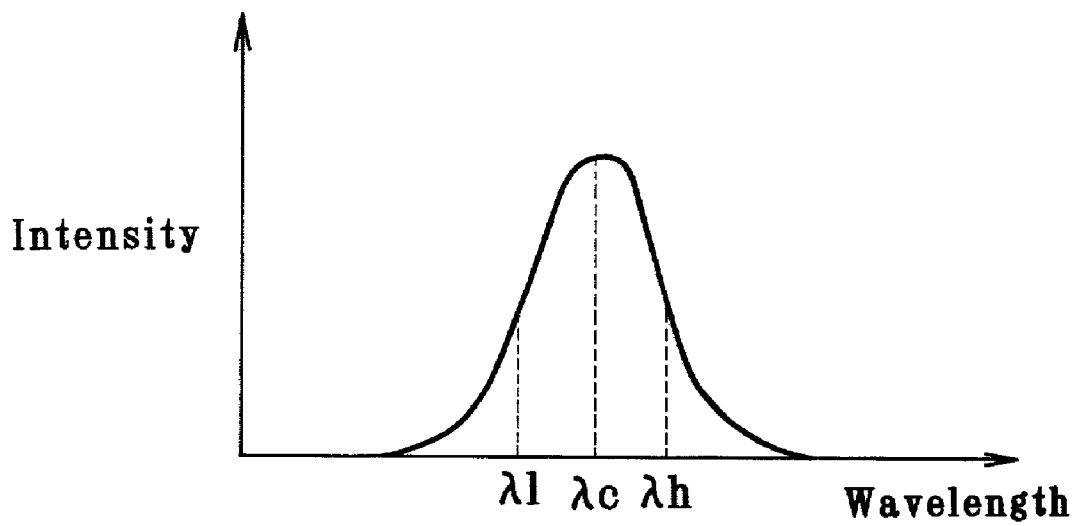
FIGS. 10(a) and 10(b) are diagrams showing the spectral distribution of a low-coherence light source and the dispersion characteristics of an optical element.
Figure 10B:
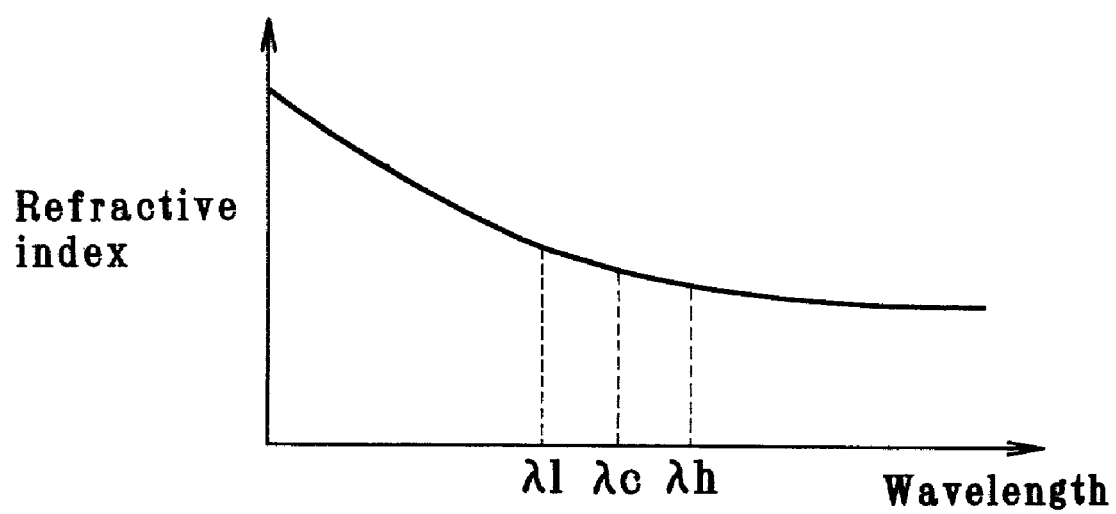
Figure 11:
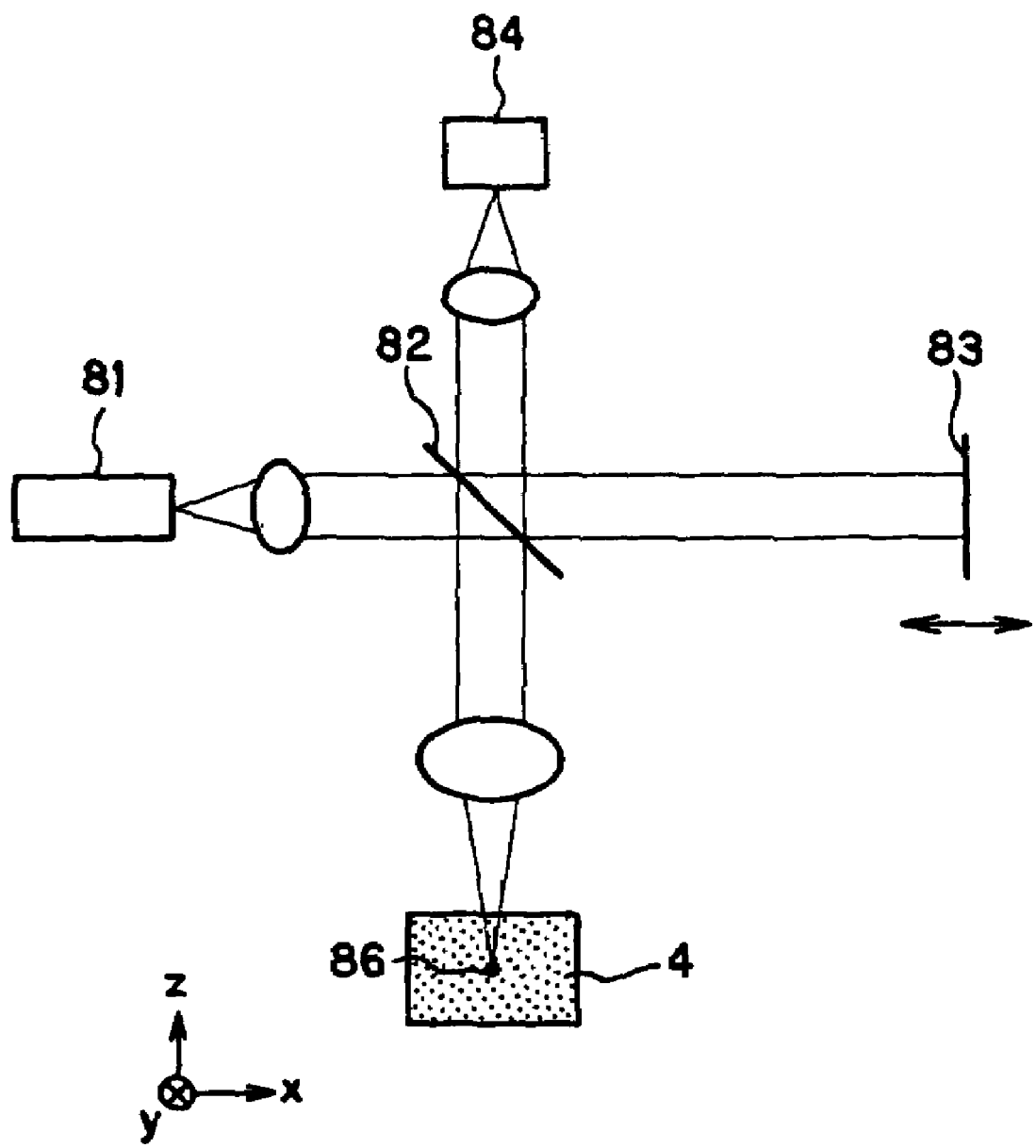
FIG. 11 is a diagram showing a general optical system for low-coherence interferometry.

Let us consider a case where light having a spectral width of certain size is used as light from the light source. When the light passes through an optical element placed in the optical path, the optical path length of the light differs for different wavelengths according to the dispersion characteristics of the optical element. For example, if the spectral distribution of the light source is as shown in FIG. 10(a), when light from the light source passes through an optical element having dispersion characteristics as shown in FIG. 10(b), the optical path length of light of wavelength $\lambda l$ shown in FIGS. 10(a) and 10(b) becomes longer than the optical path length of light of wavelength $\lambda h$. When interferometric measurement is carried out with the optical system or optical apparatus according to the present invention, if the optical path length differs for different wavelengths, the S/N ratio degrades. A difference in dispersion characteristics between the signal light path and the reference light path is produced as a result of changing the optical system in the signal light path performed by the beam diameter changing optical system and the correcting mechanism or an operation of varying the numerical aperture (effective numerical aperture) of the objective. Accordingly, the use of the above-described dispersion adjusting element makes it possible to compensate for the difference in dispersion characteristics between the signal light path and the reference light path. Consequently, the S/N ratio in interferometric measurement can be improved.

Further, the optical apparatus may be arranged such that a change in the optical path length due to a change in the effective numerical aperture of the objective and a change in the optical system incidental to the effective numerical aperture change is compensated by the optical path length control mechanism as an amount of optical path length adjustment made by the mechanism. The use of this arrangement makes it possible to compensate for the change in the optical path length as in the case of the above-described dispersion adjusting element.

It is preferable that the optical apparatus should have a storage device for storing either or both of the amount of dispersion adjustment and the amount of optical path length adjustment. As has been stated above, there is a method wherein the effective numerical aperture of a single objective is changed to switch between OCT and OCM. In this case, it is necessary in order to perform observation efficiently with a high S/N ratio to make either or both of the adjustment of dispersion and the adjustment of optical path length accurately in accordance with the change of the effective numerical aperture. On the other hand, it is necessary to change a variety of objectives from one to another in order to observe various samples at optimum magnifications. In this case, the effective numerical aperture also changes variously. Accordingly, there are a large number of combinations of the amount of dispersion adjustment and the amount of optical path length adjustment to be made in accordance with the change of the effective numerical aperture.

It is very troublesome in performing an observation operation to find an optimum amount of adjustment to be made every time the effective numerical aperture changes. Therefore, if either or both of the amount of dispersion adjustment and the amount of optical path length adjustment are previously stored in a storage device, the stored data can be referenced during the operation of adjusting the dispersion and/or the optical path length.

The light source is preferably a low-coherence light source. If the optical apparatus has a low-coherence light source, low-coherence interferometric observation can be performed.

It is possible to construct a microscope having the optical system according to the present invention. If the foregoing optical system is incorporated into or connected to a microscope, it is possible to perform efficient observation making use of the operability of the microscope system.

The foregoing optical system may be arranged to be detachably connected to a microscope. With this arrangement, the optical system can be added to a conventional microscope without newly constructing a microscope system. It also becomes possible to attach a single optical system to a plurality of different microscopes.

As has been stated above, the optical system and optical apparatus according to the present invention can minimize the time needed for image acquisition in observation by either OCT or OCM. Accordingly, when a biological sample is observed in vivo, in particular, the optical system and optical apparatus according to the present invention can meet the need to observe the motion of cells and tissues at high time resolution. In addition, the S/N ratio is not degraded when the OCT and OCM observation modes are switched from one to another.

Examples of the optical system and optical apparatus according to the present invention will be described below with reference to the accompanying drawings.

EXAMPLE 1

Figure 5A:
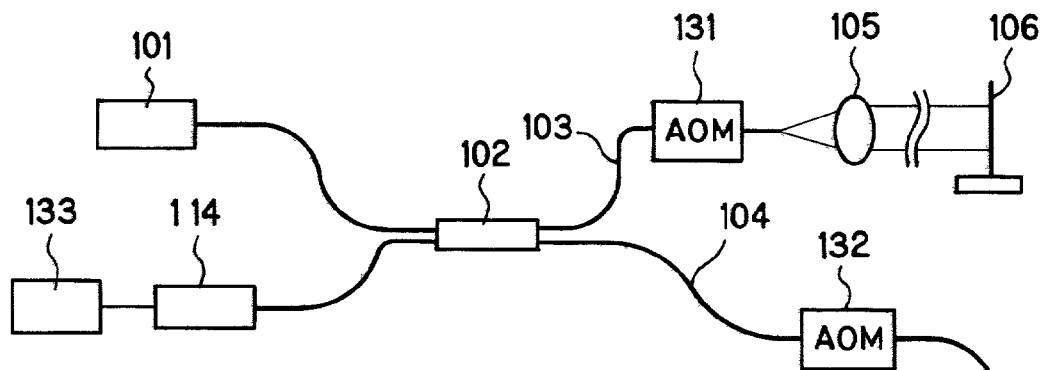

FIG. 5(a) shows an example of the optical system according to the present invention. This is an example of a low-coherence interferometric optical system for observing an image of a section in a sample that is parallel to the optical axis of the objective.

In FIG. 5(a), light from a low-coherence light source 101 is guided to a fiber coupler 102 through an optical fiber. Light from the fiber coupler 102 is branched into a reference light path 103 and a signal light path 104. Light in the reference light path 103 passes through an AOM (acoustooptic modulator) 131 and is formed into parallel rays of light through a collimator lens 105 and then reflected by a movable mirror 106. The reflected light from the movable mirror 106 passes through the collimator lens 105 and returns through the same optical path to reach the fiber coupler 102 through the AOM 131.

Meanwhile, light in the signal light path 104 passes through an AOM 132 and exits from a single-mode fiber end 191. The emergent light is formed into parallel rays of light through a collimator lens 107 and then reflected by a galvanometer mirror 108 for scanning in the x-direction. The reflected light passes through a pupil relay optical system 109 in a beam diameter changing optical system 115 and is applied to a sample 111 through an objective 110. Scattered light from an observation point 112 in the sample 111 passes through the objective 110, the pupil relay optical system 109, the galvanometer mirror 108, the collimator lens 107 and the AOM 132 to reach the fiber coupler 102. Light returning from the reference light path 103 and light returning from the signal light path 104 are combined together in the fiber coupler 102 and detected by a photodetector 114. The output of the photodetector 114 is input to a signal processor 133. In this optical system, the light-branching element and the light-combining element are formed from a single fiber coupler 102.

In this example, the optical path length control mechanism is formed from the collimator lens 105, the movable mirror 106 and a moving mechanism (not shown) for moving the movable mirror 106. By moving the movable mirror 106 at high speed, a Doppler shift is produced in the frequency of light. By operating the AOMs 132 and 133, the frequency of light in each optical path is modulated. These operations can be used selectively or in combination. A signal having a difference frequency component corresponding to the frequency difference between light passing through the reference light path 103 and light passing through the signal light path 104 is detected by the signal processor 133, whereby heterodyne interferometric measurement can be performed utilizing the frequency difference between the reference light path 103 and the signal light path 104.

Next, the operation of the signal light path will be described. The pupil 113 of the objective 110 is relayed by the pupil relay optical system 109. The galvanometer mirror 108 is disposed at the conjugate position of the pupil 113 relayed by the pupil relay optical system 109.

Figure 5B:
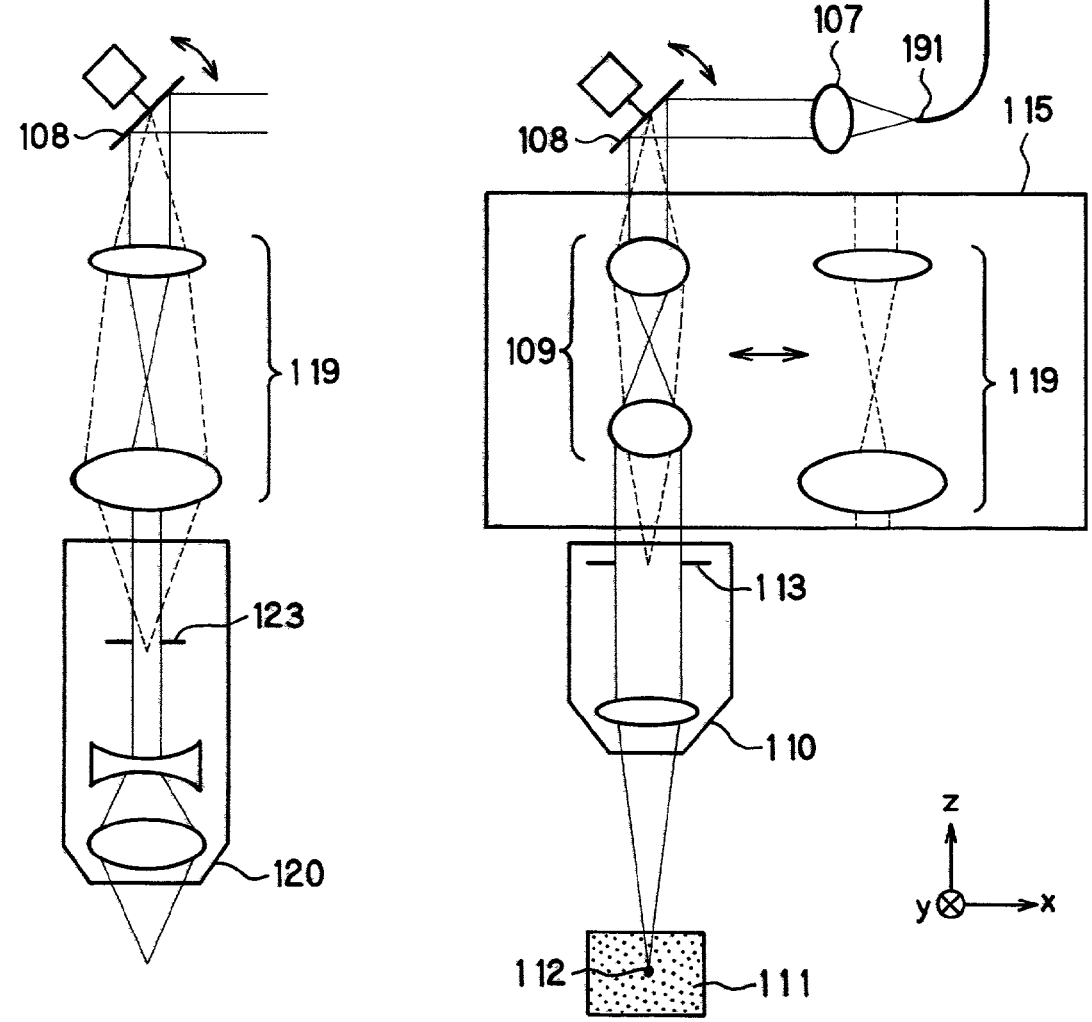

The objective 110 has a large depth of focus, that is, a small numerical aperture. On the other hand, an objective 120 shown in FIG. 5(b) has a large numerical aperture. FIG. 5(b) illustrates the arrangement of the optical system shown in FIG. 5(a), in which the objective 110 has been switched to the objective 120. In FIG. 5(b), a part of the optical system including the galvanometer mirror 108 through the objective 120 is shown. Thus, when OCT observation is performed, the objective 110 is used. When OCM observation is performed, the objective 120 is used, and observation can be performed with a confocal optical system using the single-mode fiber end 191 as a confocal pinhole.

The diameter of the pupil 123 of the objective 120 is smaller than the diameter of the pupil 113 of the objective 110. Therefore, when the objective 120 is used, the pupil relay optical system 109 is changed to another pupil relay optical system 119 by the beam diameter changing optical system 115. The magnification for the pupil relay from the galvanometer mirror 108 to the pupil of the objective is set so that the pupil relay magnification is smaller through the pupil relay optical system 119 than through the pupil relay optical system 109. Accordingly, the beam diameter of light emerging from the galvanometer mirror 108 can be made coincident with the pupil diameter of the objective. Thus, light from the light source 101 can be used efficiently without waste.

The position of the pupil 123 within the objective 120 is different from that of the objective 110. However, the pupil 123 is made conjugate to the galvanometer mirror 108 by the pupil relay optical system 119. In other words, in this example, the position of the relayed pupil of the objective is substantially coincident with the galvanometer mirror 108. Thus, the beam diameter changing optical system 115 also functions as a correcting mechanism.

EXAMPLE 2

Figure 6A:
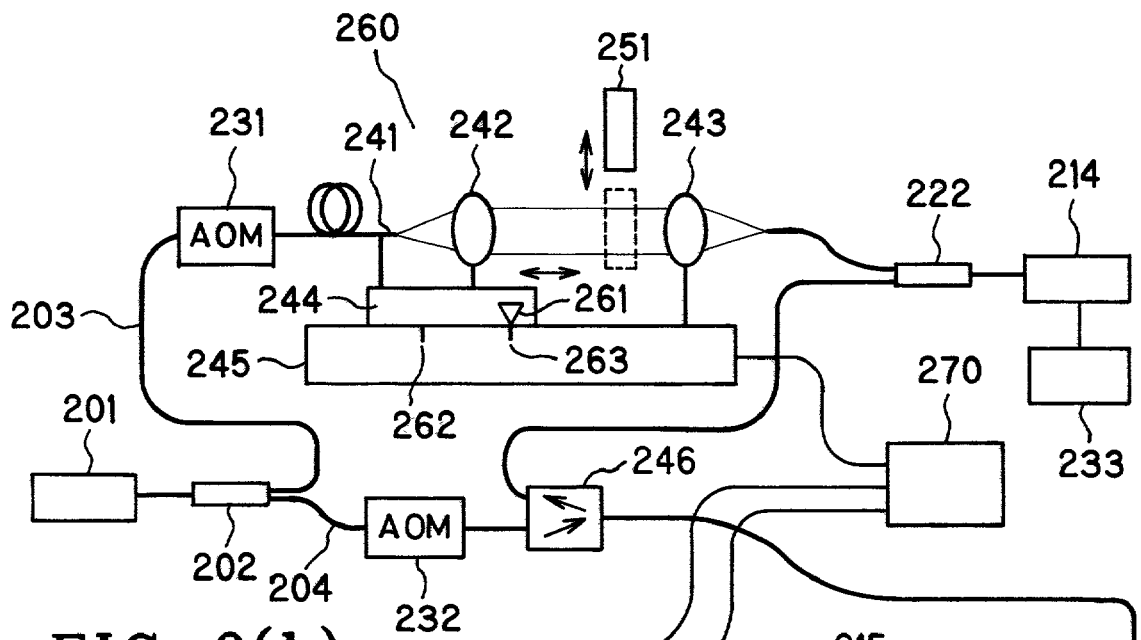

FIG. 6(a) shows an example of the optical apparatus according to the present invention. This is an example of a low-coherence interferometric optical apparatus for observing an image of a section in a sample that is parallel to the optical axis of the objective.

In FIG. 6(a), light from a low-coherence light source 201 is guided to a fiber coupler 202 through an optical fiber. Light from the fiber coupler 202 is branched into a reference light path 203 and a signal light path 204. Light in the reference light path 203 passes through an AOM 231 and exits from a fiber end 241. Thereafter, the light is formed into parallel rays of light through a collimator lens 242 and guided to a fiber coupler 222 through another collimator lens 243.

Meanwhile, light in the signal light path 204 passes through an AOM 232 and a circulator 246 and exits from a single-mode fiber end 291. The emergent light is formed into parallel rays of light through a collimator lens 207. Thereafter, the light passes through a beam diameter changing optical system 215 and is then reflected by a galvanometer mirror 208 for scanning in the x-direction. The reflected light passes through a pupil relay optical system 209 and is applied to a sample 211 through an objective 210. The sample 211 is held on a stage 216 movable in the z-direction. Scattered light from an observation point 212 in the sample 211 passes through the objective 210, the pupil relay optical system 209, the galvanometer mirror 208, the beam diameter changing optical system 215 and the collimator lens 207 to reach the fiber coupler 222 through the circulator 246. Light from the reference light path 203 and light from the signal light path 204 are combined together in the fiber coupler 222 and detected by a photodetector 214. The output of the photodetector 214 is input to a signal processor 233.

First, the operation of the signal light path will be described. In this example, the low-coherence light source 201 has a center wavelength of 1.3 μm and a coherence length of 20 μm. The objective 210 shown in FIG. 6(a) has a numerical aperture of 0.5. In this case, Lc=20 μm Df=5.2 μm Hence, the objective 210 satisfies the condition of Lc≧Df.

In FIG. 6(a), the beam diameter of light entering the objective 210 is coincident with the diameter of the pupil 213 of the objective 210. Therefore, the effective numerical aperture is equal to the numerical aperture of the objective 210. Accordingly, when the optical system is in this state, observation by OCM can be performed. Under these circumstances, a scanning control mechanism 270 chooses the stage 216 as a scanning mechanism for the first direction (z-direction) and sets the oscillation frequency at 10 Hz. Further, the oscillation frequency of the galvanometer mirror 208, which is a scanning mechanism for the second direction (x-direction), is set at 4 kHz.

In the optical apparatus according to this example, the observation range is 400 μm in the x-direction and 400 μm in the z-direction, and the scanning time per image in the xz-section is set at 0.1 second. Assuming that the number of pixels obtained is 400 by 400 pixels, the above-described oscillation frequencies as converted into average scanning speeds are 3.2 m/sec.(=v2) in the x-direction and 8 mm/sec. (=v1) in the z-direction, respectively. Hence, v2>v1. In other words, high-speed scanning is performed in the x-direction, and scanning in the z-direction is performed at relatively low speed, thereby obtaining an xz-section image. Regarding the measurement of an interference signal, heterodyne measurement is carried out using the difference frequency between the modulation frequencies of the AOMs 231 and 232 placed in the reference light path and the signal light path, respectively. Detection of the difference frequency component is performed by the signal processor 233.

Figure 6B:
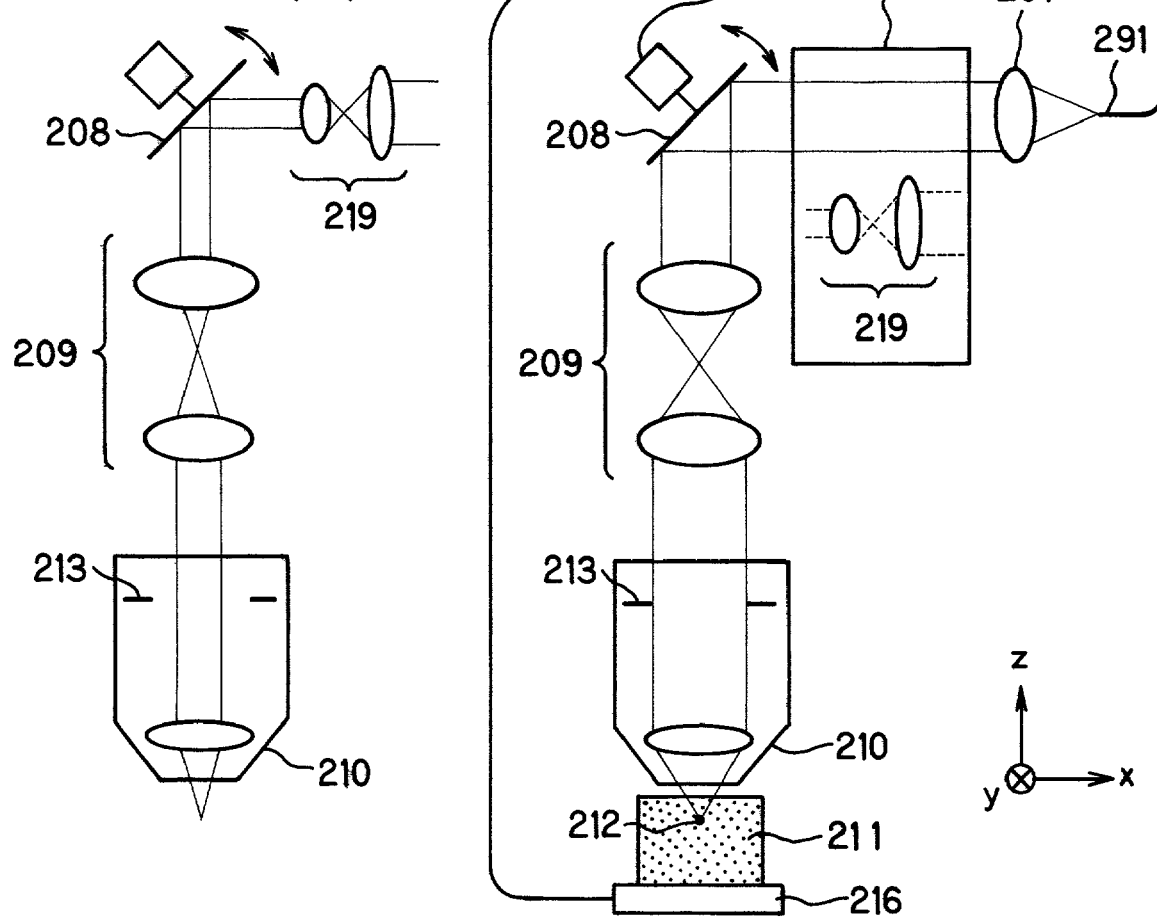

FIG. 6(b) shows an example in which OCT observation is performed by using the same objective 210 as in FIG. 6(a). In FIG. 6(b), a part of the optical system shown in FIG. 6(a) behind the collimator lens 207 is extractively shown. The beam diameter changing optical system 215 has a beam diameter changing optical system unit 219. The mechanism is arranged such that the beam diameter changing optical system unit 219 can be inserted in the optical path between the collimator lens 207 and the galvanometer mirror 208. The beam diameter changing optical system unit 219 has a magnification for reducing the beam diameter of parallel rays of light emerging from the collimator lens 207. For example, the magnification is set so that when the beam diameter changing optical system unit 219 is inserted into the optical path, the effective numerical aperture of the objective 210 becomes 0.035. In this case, Df' is as follows:

Df'=about 1 mm

Hence, the optical system shown in FIG. 6(b) satisfies the condition of Lc<Df'.

In OCT observation with the optical system shown in FIG. 6(b), the scanning time per image in the xz-section is also set at 0.1 second. In OCT, generally, scanning in the first direction (z-direction) is performed by using the movable mirror 106 in FIG. 5(a), for example, which oscillates at high speed, and heterodyne measurement utilizing a Doppler frequency produced at this time is frequently performed. In this example, however, heterodyne measurement using modulation frequencies produced in the AOMs 231 and 232 is also performed in OCT. Therefore, high-speed scanning in the z-direction is not needed. Accordingly, the scanning control mechanism 270 sets the scanning speed v1 in the first direction and the scanning speed v2 in the second direction so that the condition of v2>v1 is satisfied, as in the case of FIG. 6(a).

With the above-described scanning speed settings, scanning in the second direction can be performed by driving the same galvanometer mirror 208 as used in FIG. 6(a) at the same scanning speed as in the case of FIG. 6(a). Thus, the control mechanism for the galvanometer mirror 208 can be simplified. Regarding the scanning mechanism for the first direction, the stage 216 or the optical path length control mechanism 260 in the reference light path can be used. When the stage 216 is used, the optical path length control mechanism 260 needs no scanning mechanism, advantageously.

Thus, in this example, all of the objective, the x-direction scanning mechanism and scanning speed, the z-direction scanning mechanism and the light modulators for heterodyne measurement can be used in common between OCT and OCM observation operations.

Next, the optical path length control mechanism 260 in the reference light path will be described. Principal constituent elements of the optical path length control mechanism 260 are collimator lenses 242 and 243, a driving stage 245, and a driving unit 244. The fiber end 241 and the collimator lens 242 are secured to the driving unit 244. The driving unit 244 moves on the driving stage 245. This causes a change in the optical path length between the collimator lenses 242 and 243. Thus, the optical path length is controlled.

When the optical system for OCM shown in FIG. 6(a) and the optical system for OCT shown in FIG. 6(b) are to be switched from one to another, the beam diameter changing optical system unit 219 is inserted into or removed from the optical path in the beam diameter changing optical system 215. The insertion or removal of the beam diameter changing optical system unit 219 causes a new change in the optical path length. An optical path length change may cause the observation point to differ to a considerable extent between OCM and OCT. There is also a possibility that the observation point 212 may be out of the sample 211. To eliminate these possibilities, it is necessary to make some optical compensation.

Therefore, the driving unit 244 in the optical path length control mechanism 260 is moved through a distance corresponding to the change in the optical path length, whereby the influence of the optical path length change can be eliminated. In this example, as a device for storing the amount of optical path length adjustment, an indicating mark 261 is put on the driving unit 244, and scale marks 262 and 263 for adjustment are put on the driving stage 245. Therefore, the amounts of optical path length adjustment can readily be switched from one to another.

Further, the optical apparatus is arranged so that a dispersion adjusting element 251, e.g. a prism or a diffraction grating, can be inserted into and removed from the optical path between the collimator lenses 242 and 243. The dispersion adjusting element 251 compensates for a difference in dispersion characteristics that may be produced between the signal light path and the reference light path. It should be noted that the difference in dispersion characteristics is produced by insertion and removal of the beam diameter changing optical system unit 219 into and from the signal light path. The provision of the dispersion adjusting element 251 makes it possible to prevent degradation of the S/N ratio which would otherwise be caused by switching between the optical systems.

In this example, the scanning control mechanism 270, the beam diameter changing optical system 215, the optical path length control mechanism 260 and the dispersion adjusting element 251 may be electrically controlled so that troublesome operations related to switching between OCT and OCM can be all automatically performed.

EXAMPLE 3

Figure 7A:
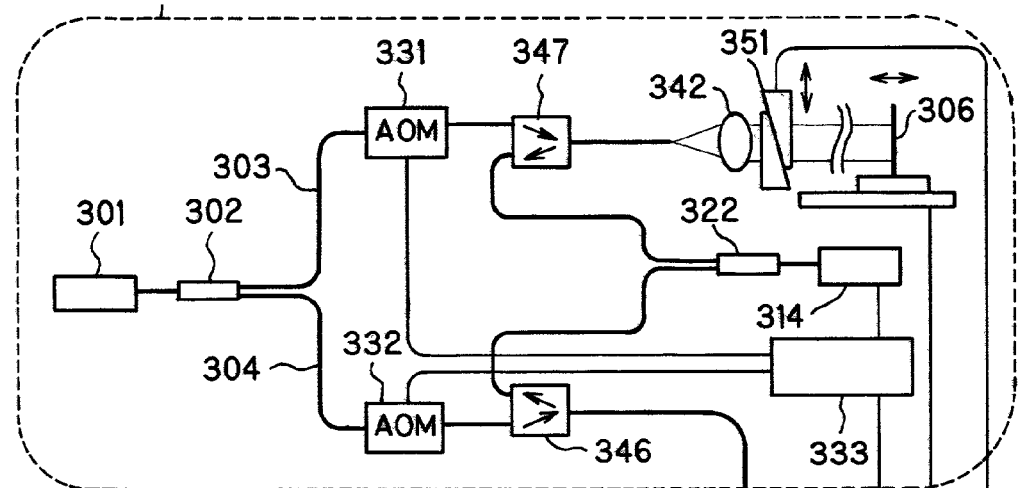

FIG. 7(a) shows another example of the optical apparatus according to the present invention. This is also an example of a low-coherence interferometric optical apparatus for observing a three-dimensional image within a sample.

In FIG. 7(a), light from a low-coherence light source 301 is guided to a fiber coupler 302 through an optical fiber. Light from the fiber coupler 302 is branched into a reference light path 303 and a signal light path 304. Light in the reference light path 303 passes through an AOM 331 and a circulator 347 and is formed into parallel rays of light through a collimator lens 342. Further, the light passes through a dispersion adjusting element 351 and is reflected by a movable mirror 306. The reflected light passes through the dispersion adjusting element 351, the collimator lens 342 and the circulator 347 to reach a fiber coupler 322.

Meanwhile, light in the signal light path 304 passes through an AOM 332 and a circulator 346 and exits from a single-mode fiber end 391. The emergent light passes through a collimator lens 307 and is reflected by a galvanometer mirror 318. The reflected light passes through a pupil relay optical system 319 and is incident on a galvanometer mirror 308. The reflected light from the galvanometer mirror 308 passes through a pupil relay optical system 309 before being applied to a sample 311 through an objective 310. The sample 311 is held on a stage 316.

Scattered light from an observation point 312 in the sample 311 passes through the objective 310, the pupil relay optical system 309, the galvanometer mirror 308, the pupil relay optical system 319, the galvanometer mirror 318 and the collimator lens 307 to reach the fiber coupler 322 through the circulator 346. Light from the reference light path 303 and light from the signal light path 304 are combined together in the fiber coupler 322 and detected by a photodetector 314. The output of the photodetector 314 is input to a signal processor 333.

In this example, the low-coherence light source 301 has a center wavelength of 1.3 µm and a coherence length of 20 µm. The objective 310 has a numerical aperture of 0.5. In FIG. 7(a), the objective 310 forms an optical system for OCM observation. In this case, Lc=20 µm Df=5.2 µm Hence, the objective 310 satisfies the condition of Lc≧Df.

Figure 7B:
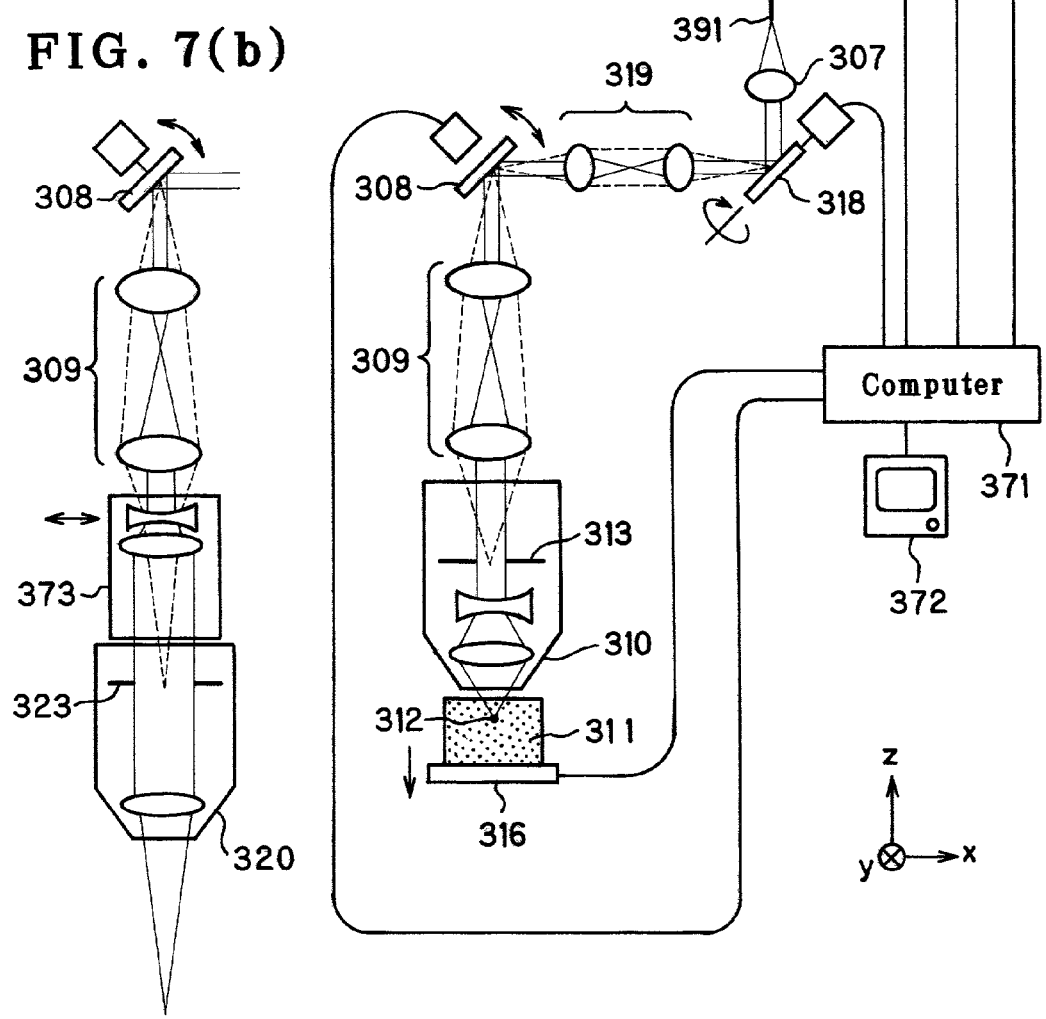

FIG. 7(b) shows a part of an optical system for OCT observation. In FIG. 7(b), a part of the optical system shown in FIG. 7(a), which includes the galvanometer mirror 308 through the objective 320, is extractively shown. The numerical aperture of the objective 320 is 0.025. In this case, Df is as follows:

Df=about 2 mm

Hence, the objective 320 satisfies the condition of Lc<Df.

In this example, the optical apparatus has the galvanometer mirrors 308 and 318 for scanning in the second direction (x-direction) and the third direction (y-direction), respectively. For scanning in the first direction (z-direction), the stage 316 or the optical path length control mechanism (movable mirror 306) is used. Accordingly, three-dimensional observation can be performed in both OCT and OCM observation modes.

The objectives 310 and 320 in this example differ from each other in the pupil diameter and pupil position of their pupils 313 and 323. When the pupil position of the objective and the scanning mirror position are not in conjugate relation to each other, the light beam may be eclipsed, as has been stated above. In this example, therefore, when the objective 320 is used, an adapter lens (beam diameter changing optical system) 373 is positioned between the pupil relay optical system 309 and the objective 320 to make the beam diameter and the pupil diameter coincide with each other. This arrangement is advantageous in that the pupil relay optical system 309 need not be changed.

The optical apparatus is set so that in OCT observation shown in FIG. 7(b) a two-dimensional image of the xz-section is observed, and a region of interest in the two-dimensional image is three-dimensionally observed in the OCM observation mode shown in FIG. 7(a). First, in OCT observation, the objective 320 is used, and the adapter lens 373 is inserted into the optical path. Scanning in the first direction is performed by using the movable mirror 306 in the reference light path 303. Scanning in the second direction is performed by using the scanning mirror 308. In the OCT observation, the scanning speed in the first direction is set faster than the scanning speed in the second direction to perform heterodyne interferometric measurement utilizing the Doppler shift of the light frequency produced by the scanning performed with the movable mirror 306. The operation of setting the scanning speeds is controlled by a computer 371 serving as a scanning control mechanism.

Next, when OCM observation is to be performed, the objective 310 is inserted into the optical path, and the adapter lens 373 is removed from the optical path. Scanning in the second direction is performed with the scanning mirror 308. Scanning in the third direction is performed with the scanning mirror 318. Scanning in the first direction is performed by moving the stage 316. Acquisition of a three-dimensional image is effected by obtaining a two-dimensional image of the xy-section first and then scanning the two-dimensional image in the z-direction. Therefore, the scanning speeds are set so that scanning in the z-direction is the slowest of the three scanning operations.

The operation of switching the scanning mechanism for the first direction from the optical path length control mechanism (movable mirror 306) to the stage 316 and the operation of setting the scanning speed for each scanning mechanism are controlled by the computer 371. In the OCM observation, the AOMs 331 and 332 are used as light frequency modulating members for heterodyne interferometric measurement. In heterodyne detection in each of OCT and OCM, the Doppler frequency produced by the movable mirror 306 or the difference frequency produced by the AOMs 331 and 332 is processed in the signal processor 333. Specifically, a lock-in amplifier or the like is used. The output of the signal processor 333 is fed to the computer 371 where it is converted into an image. The image is displayed by a display unit 372.

In FIG. 7(b), when the adapter lens 373 is inserted into the optical path, there are changes in the dispersion and the optical path length due to the adapter lens 373. The change in the dispersion can be compensated by the dispersion adjusting element 351 placed in the reference light path. The adjustment of the dispersion can also be controlled by the computer 371. It should be noted that the dispersion adjusting element 351 should preferably be arranged as shown in FIG. 7(a). That is, wedge prisms are placed to face each other to form the dispersion adjusting element 351, whereby the amount of dispersion adjustment made by the dispersion adjusting element 351 can be controlled continuously. When an objective or a sample is changed to another, there may be a difference in dispersion characteristics between the reference light path 303 and the signal light path 304. With this arrangement, however, any slight difference in dispersion characteristics can be adjusted so as to be canceled.

In FIG. 7(a), the stage 316 is used as a mechanism for scanning in the z-direction in OCM observation, that is, for scanning the observation point 312 in the first direction. It is also possible to scan the objective 310 in the z-direction, for example, as another method for scanning the observation point 312 in the first direction. Such an arrangement is useful in a case where it is difficult to place the sample 311 on the stage 316, or in a case where the sample 311 is a biological sample and cannot be moved for scanning. In this case, however, as the objective 310 is moved for scanning in the z-direction, the optical path length of the signal light path changes. Therefore, it is necessary to move the movable mirror 306 simultaneously in synchronism with the scanning movement of the objective 310.

EXAMPLE 4

FIGS. 8(a) and 8(b) show an example in which the position of the relayed pupil is corrected. In this example, objectives used in OCT and OCM, respectively, are equal in the pupil diameter but different in the pupil position. FIG. 8(a) shows a part of the optical system shown in FIG. 7(a). FIG. 8(b) shows the same part of the optical system as that shown in FIG. 7(b).

The pupil 413 of an objective 410 and the pupil 423 of an objective 420 have the same pupil diameter. However, the pupil positions of the objectives 410 and 420 are different from each other. In this example, a plane-parallel plate 473 is inserted into and removed from the optical path as shown in FIGS. 8(a) and 8(b) as a correcting mechanism for making the pupil position and the galvanometer mirror conjugate to each other. The plane-parallel plate 473 may be made of a glass, crystal, transparent resin, or other similar material. With this arrangement, objectives can be switched from one to another simply by using a relatively simple optical element without the need to change the pupil relay optical system 409 and with substantially no change in the relative positions of the scanning mirrors, the pupil relay optical system and the sample.

EXAMPLE 5

Figure 9:
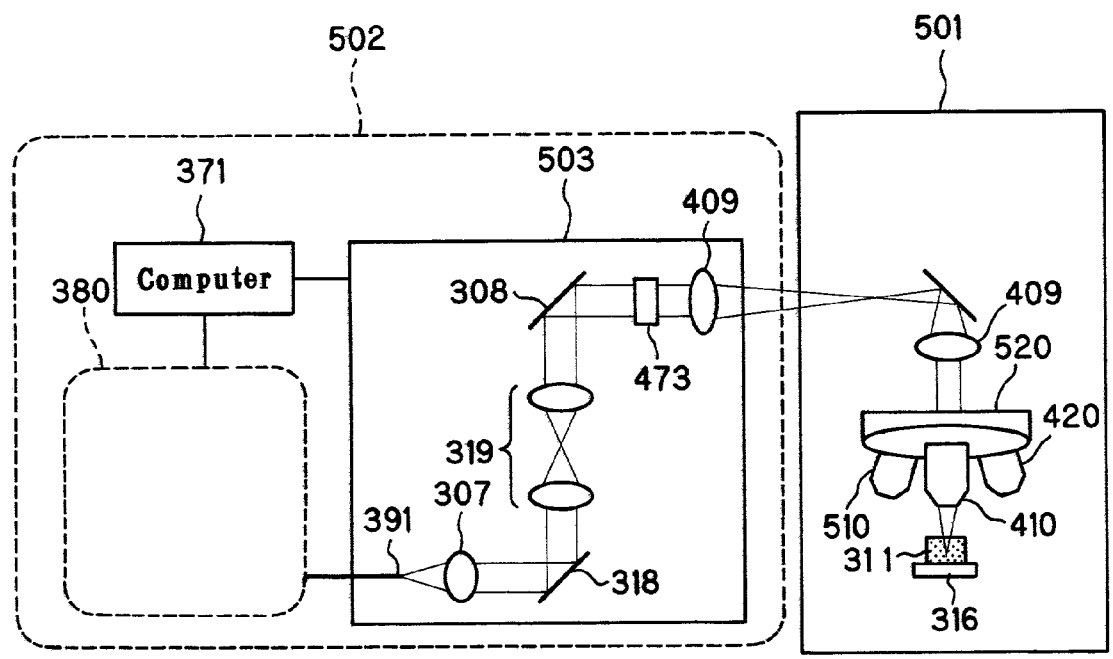
FIG. 9 is a diagram showing an example of a microscope having an optical system according to the present invention as Example 5.

FIG. 9 shows an example in which the optical system according to the present invention is combined with a microscope. In FIG. 9, the optical system used in the optical apparatus shown in FIGS. 7(a) and 8(a) is applied to a microscope. In FIG. 9, the signal light path in the interference optical system 380 shown in FIG. 7(a) is introduced into a scanning optical system 503, and light from the scanning optical system 503 enters a microscope 501. The scanning optical system 503 comprises the optical system shown in FIG. 8(a).

The microscope 501 has a revolver 520. The objectives 410 and 420 used in FIGS. 8(a) and 8(b), together with another objective 510, are mounted on the revolver 520. Rotation of the revolver 520 allows the objectives 410, 420 and 510 to be changed from one to another to perform OCT or OCM observation selectively.

The interference optical system 380 and the scanning optical system 503 can be controlled by the computer 371. Further, the interference optical system 380 and the scanning optical system 503 can be integrally arranged as a scanning interference optical unit 502. The scanning interference optical unit 502 is arranged to be removably attached to the microscope 501. Accordingly, the scanning interference optical unit 502 can be attached to a variety of microscopes suitable for various observation applications.

As will be clear from the foregoing description, the optical system and optical apparatus according to the present invention allow the OCT and OCM observation modes to be readily switched from one to another and enable optimum and efficient observation to be performed in each of the OCT and OCM modes. In addition, when the OCT and OCM modes are switched from one to another to perform observation, it is possible to prevent degradation of the S/N ratio due to switching between the two observation modes and to attain a high S/N ratio in both the OCT and OCM observation modes.

I claim:

1. An optical apparatus comprising:
   a light source;
   a light-branching member having a boundary surface for branching light from said light source into a reference light path and a signal light path;
   at least one objective placed in said signal light path;
   a scanning system for moving light collected by said objective and a sample relative to each other;
   a light-combining member having a boundary surface for combining together said reference light path and said signal light path;
   a light-detecting element for detecting light combined by said light-combining member;
   an optical path length control mechanism placed between said light-branching member and said light-combining member to vary an optical path length; and
   a scanning control mechanism;
   wherein said scanning system has, at least, a first scanning mechanism for moving said collected light and said sample relative to each other in a first direction parallel to an optical axis of said objective, and a second scanning mechanism for moving said collected light and said sample relative to each other in a second direction perpendicular to said first direction; and wherein said scanning control mechanism has a function of choosing between said first scanning mechanism and said optical path length control mechanism, and a function of determining a scanning speed of the chosen mechanism and a scanning speed of said second scanning mechanism.

2. An optical apparatus according to claim 1, wherein an objective of said at least one objective is structure to be placed in said signal light path and has a numerical aperture that satisfies a condition of $Lc \geq Df$ where Df is a value generally known as depth of focus, which is obtained from $Df = \lambda c/(NA)^2$ where NA is a numerical aperture of the objective, and $\lambda c$ is a center wavelength of the light source, and Lc is a coherence length of light incident on the sample.

3. An optical apparatus according to claim 2, wherein an objective of said at least one objective is structural to be placed in said signal light path and has a numerical aperture that satisfies a condition of $Lc < Df$, where Df is a value generally known as depth of focus, which is obtained from $Df = \lambda c/(NA)^2$, where NA is a numerical aperture of the objective, and $\lambda c$ is a center wavelength of the light source, and Lc is a coherence length of light incident on the sample.

4. An optical apparatus according to claim 3, wherein said scanning control mechanism selectively changes choice between said first scanning mechanism and said optical path length control mechanism and determination of the scanning speed of said chosen mechanism and the scanning speed of said second scanning mechanism in accordance with switching between said objectives.

5. An optical apparatus according to claim 4, wherein said scanning control mechanism sets said scanning speeds as follows:
   when $Lc < Df$, $v1 > v2$;
   when $Lc \geq Df$, $v2 > v1$;
   where Df is a value obtained from $Df = \lambda c/(NA)^2$, where NA is a numerical aperture of an objective placed in the signal light path, and $\lambda c$ is a center wavelength of the light source; Lc is a coherence length of light incident on the sample; and v1 and v2 are a scanning speed in the first direction and a scanning speed in the second direction, respectively.

6. An optical apparatus according to claim 3, wherein said scanning control mechanism sets said scanning speeds as follows:
   when $Lc < Df'$, $v1 > v2$;

when $Lc \geq Df'$, $v2>v1$;
where $Df'$ is a value obtained from $Df'=\lambda c/(NA')^2$, where $NA'$ is an effective numerical aperture of an objective placed in the signal light path, and $\lambda c$ is a center wavelength of the light source; Lc is a coherence length of light incident on the sample; and v1 and v2 are a scanning speed in the first direction and a scanning speed in the second direction, respectively.

7. An optical apparatus according to claim 4, further comprising:
a frequency modulating member provided in at least either one of said reference light path and said signal light path, said frequency modulating member having a function of modulating a frequency of light without causing a change in optical path length;
wherein said scanning control mechanism sets said scanning speeds so that the following condition is satisfied regardless of a size relation between Lc and Df or between Lc and Df':
$v2>v1$
where Df and Df' are values generally known as depth of focus, Df being obtained from $Df=\lambda c/(NA)^2$, where NA is a numerical aperture of an objective, $\lambda c$ is a center wavelength of the light source, Df' being obtained from $Df'=\lambda c/(NA')^2$, where NA' is an effective numerical aperture of an objective, and $\lambda c$ is a center wavelength of the light source; Lc is a coherence length of light incident on the sample; and v1 and v2 are a scanning speed in the first direction and a scanning speed in the second direction, respectively.

8. An optical apparatus according to claim 4, wherein said scanning system has a third scanning mechanism for moving said collected light and said sample relative to each other in a direction perpendicular to both said first direction and said second direction, and said scanning control mechanism sets scanning speeds as follows:
when $Lc<Df$, $v1>v2>v3$;
when $Lc \geq Df$, $v2>v3>v1$;
where Df is a value obtained from $Df=\lambda c/(NA)^2$, where NA is a numerical aperture of an objective placed in the signal light path, and .mu.c is a center wavelength of the light source; Lc is a coherence length of light incident on the sample; and v1, v2 and v3 are a scanning speed in the first direction, a scanning speed in the second direction and a scanning speed in the third direction, respectively.

9. An optical apparatus according to claim 3, wherein said scanning system has a third scanning mechanism for moving said collected light and said sample relative to each other in a direction perpendicular to both said first direction and said second direction, and said scanning control mechanism sets scanning speeds as follows:
when $Lc<Df'$, $v1>v2>v3$;
when $Lc \geq Df'$, $v2>v3>v1$;
where Df' is a value obtained from $Df'=\lambda c/(NA')^2$, where NA is an effective numerical aperture of an objective placed in the signal light path, and $\lambda c$ is a center wavelength of the light source; Lc is a coherence length of light incident on the sample; and v1, v2 and v3 are a scanning speed in the first direction, a scanning speed in the second direction and a scanning speed in the third direction, respectively.

10. An optical apparatus according to claim 4, wherein said scanning system has a third scanning mechanism for moving said collected light and said sample relative to each other in a direction perpendicular to both said first direction and said second direction;
said optical apparatus further comprising:
a frequency modulating member provided in at least either one of said reference light path and said signal light path, said frequency modulating member having a function of modulating a frequency of light without causing a change in optical path length.

11. An optical apparatus according to claim 10, wherein said scanning control mechanism sets scanning speeds in accordance with a numerical aperture or effective numerical aperture of an objective to be used, as follows:
when $Lc<Df$ or $Lc<Df'$, $v2>v1>v3$ or $v2>v3>v1$;
when $Lc \geq Df$ or $Lc \geq Df'$, $v2>v3>v1$;
where Df is a value obtained from $Df=\lambda c/(NA)^2$, where NA is a numerical aperture of an objective placed in the signal light path, and $\lambda c$ is a center wavelength of the light source; Df' is a value obtained from $Df'=\lambda c/(NA')^2$, where NA' is an effective numerical aperture of an objective placed in the signal light path, and $\lambda c$ is a center wavelength of the light source; Lc is a coherence length of light incident on the sample; and v1, v2 and v3 are a scanning speed in the first direction, a scanning speed in the second direction, and a scanning speed in the third direction, respectively.

12. An optical apparatus according to claim 2, further comprising:
a dispersion adjusting element for compensating for a difference in dispersion characteristics between said signal light path and said reference light path produced by a change in an effective numerical aperture of said objective and a change in the optical system incidental to said change, said dispersion adjusting element being capable of selectively or continuously controlling an amount of dispersion adjustment made by it.

13. An optical apparatus according to claim 2,
wherein a change in optical path length due to a change in an effective numerical aperture of said objective and a change in the optical system incidental to said change is compensated by said optical path length control mechanism as an amount of optical path length adjustment made by said optical path length control mechanism.

14. An optical apparatus according to claim 1, wherein an objective of said at least one objective is structural to be placed in said signal light path and has a numerical aperture that satisfies a condition of $Lc<Df$, where Df is a value generally known as depth of focus, which is obtained from $Df=\lambda c/(NA)^2$, where NA is a numerical aperture of the objective, and $\lambda c$ is a center wavelength of the light source, and Lc is a coherence length of light incident on the sample.

* * * * *